United States Patent
Swiatek-de Lange et al.

(10) Patent No.: US 10,815,517 B2
(45) Date of Patent: Oct. 27, 2020

(54) USE OF DPPIV/SEPRASE AS A MARKER FOR CANCER

(75) Inventors: Magdalena Swiatek-de Lange, Penzberg (DE); Johann Karl, Peissenberg (DE); Wolfgang Rollinger, Rott (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/268,042

(22) Filed: Oct. 7, 2011

(65) Prior Publication Data

US 2012/0021929 A1 Jan. 26, 2012

Related U.S. Application Data

(63) Continuation of application No. PCT/EP2010/002544, filed on Apr. 26, 2010.

(30) Foreign Application Priority Data

Apr. 28, 2009 (EP) .................................... 09005877
May 4, 2009 (EP) .................................... 09006097

(51) Int. Cl.
   *C12Q 1/37* (2006.01)

(52) U.S. Cl.
   CPC ....... *C12Q 1/37* (2013.01); *G01N 2800/7028* (2013.01)

(58) Field of Classification Search
   None
   See application file for complete search history.

(56) References Cited

U.S. PATENT DOCUMENTS

| | | | |
|---|---|---|---|
| 7,785,810 B2 | 8/2010 | Chen | |
| 2002/0034789 A1* | 3/2002 | Zimmermann et al. | 435/69.7 |
| 2006/0199232 A1* | 9/2006 | Tacke et al. | 435/7.23 |

FOREIGN PATENT DOCUMENTS

| | | |
|---|---|---|
| EP | 1184666 A2 | 3/2002 |
| WO | 2001/074299 A3 | 10/2001 |
| WO | 2004/057336 A3 | 7/2004 |

OTHER PUBLICATIONS

International Search Report dated Jun. 23, 2010 in PCT Application No. PCT/EP2010/002544, 6 pages.
Aksoy, Saime et al., "Human Liver Nicotinamide N-Methyltransferase cDNA Cloning, Expression, and Biochemical Characterization," The Journal of Biological Chemistry, May 20, 1994, pp. 14835-14840, vol. 269, No. 20.
Aoyama, Atsuko and Chen, Wen-Tien, "A 170-kDa membrane-bound protease is associated with the expression of invasiveness by human malignant melanoma cells," Proceedings of the National Academy of Sciences USA, Nov. 1990, pp. 8296-8300, vol. 87.
Appella, E. and Anderson, C. W., "Signaling to p53: breaking the posttranslational modification code," Pathologie et Biologie, 2000, pp. 227-245, vol. 48.
Breiman, Leo, "Random Forests," Machine Learning, 2001, pp. 5-32, vol. 45.
Buccheri, Gianfranco and Ferrigno, Domenico, "Identifying Patients at Risk of Early Postoperative Recurrence of Lung Cancer: A New Use of the Old CEA Test," The Annals of Thoracic Surgery, 2003, pp. 973-980, vol. 75.
Calabretta, Bruno et al., "Altered expression of G1-specific genes in human malignant myeloid cells," Proceedings of the National Academy of Sciences, Mar. 1986, pp. 1495-1498, vol. 83.
Calabretta, Bruno et al., "Molecular Cloning of the cDNA for a Growth Factor-inducible Gene with Strong homology to S-100, a Calcium-binding Protein," The Journal of Biological Chemistry, Sep. 25, 1986, pp. 12628-12632, vol. 201, No. 27.
Chen, Donghai et al., "Activation of EDTA-Resistant Gelatinases in Malignant Human Tumors," Cancer Reserach, Oct. 15, 2006, pp. 9977-9985, vol. 66, No. 20.
Duffy, M. J., "Clinical Uses of Tumor Markers: A Critical Review," Critical Reviews in Clinical Laboratory Sciences, 2001, pp. 225-262, vol. 38, No. 3.
Friedman, Jerome H., "Regularized Discriminant Analysis," Journal of the American Statistical Association, Mar. 1989, pp. 165-175, vol. 84, No. 405.
Fukasawa, Toshio et al., "Clinical Evaluation of Serum NSE and CEA in Primary Lung Cancer Patients," Japanese Journal of Cancer and Chemotherapy, May 1986, pp. 1862-1867, vol. 13, No. 5, Abstract in English.
Garin-Chesa, Pilar et al., "Cell surface glycoprotein of reactive stromal fibroblasts as a potential antibody target in human epithelial cancers," Proceedings of the National Academy of Sciences USA, Sep. 1990, pp. 7235-7239, vol. 87.
Ghersi, G. et al., "Seprase-DPPIV Association and Prolyl Peptidase and Gelatinase Activities of the Protease Complex," Advances in Experimental Medicine and Biology, 2003, pp. 87-94, vol. 524.
Ghersi, Giulio et al., "Regulation of Fibroblast Migration on Collagenous Matrix by a Cell Surface Peptidase Complex," The Journal of Biological Chemistry, Aug. 9, 2002, pp. 29231-29241, vol. 277, No. 32.
Ghersi, Giulio et al., "The Protease Complex Consisting of Dipeptidyl Peptidase IV and Seprase Plays a Role in the Migration and Invasion of Human Endothelial Cells in Collagenous Matrices," Cancer Rsearch, May 1, 2006, pp. 4652-4661, vol. 66, No. 9.
Giachelli, Cecilia et al., "Molecular Cloning and Characterization of 2B7, A Rat mRNA Which Distinguishes Smooth Muscle Cell Phenotypes In Vitro and is Identical to Osteopontin (Secreted Phosphorprotein 1, 2aR)," Biochemical and Biophysical Research Communications, Jun. 14, 1991, pp. 867-873, vol. 177, No. 2.
Goldstein, Leslie A. et al., "Molecular cloning of seprase: a serine integral membrane protease from human melanoma," Biochimica et Biophysica Acta, 1997, pp. 11-19, vol. 1361.

(Continued)

*Primary Examiner* — Alana Harris Dent
(74) *Attorney, Agent, or Firm* — Stinson LLP

(57) ABSTRACT

Described is a method aiding in the assessment of the presence of cancer. The method uses the soluble DPPIV/seprase protein complex (DPPIV/seprase) as a universal marker of different cancer types. Measurement of DPPIV/seprase complex can, e.g., be used in the early detection or diagnosis of cancer or in the surveillance of patients who undergo surgery.

17 Claims, 6 Drawing Sheets

Specification includes a Sequence Listing.

(56) References Cited

OTHER PUBLICATIONS

Guo, Xiaojia et al., "Identification of a Serum-inducible Messenger RNA (5B10) as the Mouse Homologue of Calcyclin: Tissue Distribution and Expression in Metastatic, ras-transformed NIH 3T3 Cells," Cell Growth & Differentiation, Jul. 1990, pp. 333-338, vol. 1.

Havre, Pamela A. et al., "The role of CD26/dipeptidyl peptidase IV in cancer," Frontiers in Bioscience, Jan. 1, 2008, pp. 1634-1645, vol. 13.

Heizmann, Claus W. and Cox, Jos A., "New perspectives on S100 proteins: a multi-function Ca2+-, Zn2+- and Cu2+-binding protein family," BioMetals, 1998, pp. 383-397, vol. 11.

Henry, Leonard R. et al., "Clinical Implications of Fibroblast Activation Protein in Patients with Colon Cancer," Clinical Cancer Research, Mar. 15, 2007, pp. 1736-1741, vol. 13, No. 6.

Kassem, Heba Sh. et al., "A Potential Role of Heat Shock Proteins and Nicotinamide N-Methyl Transferase in Predicting Response to Radiation in Bladder Cancer," International Journal of Cancer, 2002, pp. 454-460, vol. 101.

Kiefer, Michael C. et al., "The cDNA and derived amino acid sequence for human osteopontin," Nucleic Acids Research, 1989, p. 3306, vol. 17, No. 8.

Kuźnicki, Jacek and Filipek, Anna, "Purification and properties of a novel Ca2+-binding protein (10.5 kDa) from Ehrlich-ascites-tumour cells," Biochemistry Journal, 1987, pp. 663-667, vol. 247.

Kuźnicki, Jacek et al., "Calcium-binding protein from mouse Ehrlich ascites-tumour cells is homologous to human calcyclin," Biochemistry Journal, 1989, pp. 951-956, vol. 263.

Kuźnicki, J. et al., "Calcyclin as a Marker of Human Epithelial Cells and Fibroblasts," Experimental Cell Research, 1992, pp. 425-430, vol. 200.

Lee, Kyung N. et al., "A novel plasma proteinase potentiates α2-antiplasmin inhibition of fibrin digestion," Blood, May 15, 2004, pp. 3783-3788, vol. 103, No. 10.

Lee, Kyung N. et al., "Antiplasmin-cleaving enzyme is a soluble form of fibroblast activation protein," Blood, Feb. 15, 2006, pp. 1397-1404, vol. 107, No. 4.

Leonard, Debra G. B. et al., "Identification and Characterization of mRNAs Regulated by Nerve Growth Factor in PC12 Cells," Molecular and Cellular Biology, Sep. 1987, pp. 3156-3167, vol. 7, No. 9.

Merle, P. et al., "Early CYFRA 21-1 variation predicts tumor response to chemotherapy and survival in locally advanced non-small cell lung cancer patients," The International Journal of Biological Markers, pp. 310-315, vol. 19, No. 4.

Miller, M. R. et al., "Series 'ATS/ERS Task Force: Standardisation of Lung Function Testing' Standardisation of spirometry," European Respiratory Journal, 2005, pp. 319-338, vol. 26.

Miyagi, Takuya et al., "Impaired expression of proteasome subunits and human leukocyte antigens class I in human colon cancer cells," Journal of Gastroenterology and Hepatology, 2003, pp. 32-40, vol. 18.

Molina, R. et al., "Tumor Markers (CEA, CA 125, CYFRA 21-1, SCC and NSE) in Patients with Non-Small Cell Lung Cancer as an Aid in Histological Diagnosis and Prognosis Comparison with the Main Clinical and Pathological Prognostic Factors," Tumor Biology, 2003, pp. 209-218, vol. 24.

Monsky, Wayne L. et al., "A Potential Marker Protease of Invasiveness, Seprase, Is Localized on Invadopodia of Human Malignant Melanoma Cells," Cancer Research, Nov. 1, 1994, pp. 5702-5710, vol. 54.

Mueller, Susette C. et al., "A Novel Protease-docking Function of Integrin at Invadopodia," The Journal of Biological Chemistry, Aug. 27, 1999, pp. 24947-24952, vol. 274, No. 35.

Nikaido, T. et al., "Cloning and nucleotide sequence of cDNA for Ki antigen, a highly conserved nuclear protein detected with sera from patients with systemic lupus erythematosus," Clinical and Experimental Immunology, 1990, pp. 209-214, vol. 79.

O'Brien, Pamela and O'Connor, Brendan F., "Seprase: An overview of an important matrix serine protease," Biochimica et Biophysica Acta, 2008, pp. 1130-1145, vol. 1784.

Okamura, Atsushi et al., "Increased Hepatic Nicotinamide N-Methyltransferase Activity as a Marker of Cancer Cachexia in Mice Bearing Colon 26 Adenocarcinoma," Japanese Journal of Cancer Research, Jun. 1998, pp. 649-656, vol. 89.

Okamura, Tomohisa et al., "Abnormally High Expression of Proteasome Activator-γ in Thyroid Neoplasm," The Journal of Clinical Endocrinology & Metabolism, 2003, pp. 1374-1383, vol. 88, No. 3.

Oldberg, Åke et al., "Cloning and sequence analysis of rat bone sialoprotein (osteopontin) cDNA reveals an Arg-Gly-Asp cell-binding sequence," Proceedings of the National Academy of Sciences USA, Dec. 1986, pp. 8819-8823, vol. 83.

Oldberg, Åke et al., "Identification of a Bone Sialoprotein Receptor in Osteosarcoma Cells," The Journal of Biological Chemistry, Dec. 25, 1988, pp. 19433-19436, vol. 263, No. 36.

Oliver, N. S. et al., "Glucose sensors: a review of current and emerging techology," Diabetic Medicine, 2009, pp. 197-210, vol. 26.

Park, John E. et al., "Fibroblast Activation Protein, a Dual Specificity Serine Protease Expressed in Reactive Human Tumor Stromal Fibroblasts," The Journal of Biological Chemistry, Dec. 17, 1999, pp. 36505-36512, vol. 274, No. 51.

Patarca, R. et al., "Structural and Functional Studies of the Early T Lymphocyte Activation 1 (Eta-1) Gene, Definition of a Novel T Cell-dependent Response Associated with Genetic Resistance to Bacterial Infection," The Journal of Experimental Medicine, Jul. 1989, pp. 145-161, vol. 170.

Patarca, R. et al., "Differential induction of interferon γ gene expression after activation of CD4+ T cells by conventional antigen and Mls superantigen," Proceedings of the National Academy of Sciences USA, Apr. 1991, pp. 2736-2739, vol. 88.

Petitjean, A. et al., "TP53 mutations in human cancers: functional selection and impact on cancer prognosis and outcomes," Oncogene, 2007, pp. 2157-2165, vol. 26.

Pineiro-Sanchez, "Identification of the 170-kDa Melanoma Membrane-bound Gelatinase (Seprase) as a Serine Integral membrane Protease," The Journal of Biological Chemistry, Mar. 21, 1997, pp. 7595-7601, vol. 272, No. 12.

Realini, Claudio et al., "Characterization of Recombinant REGα, REGβ, and REGγ Proteasome Activators," The Journal of Biological Chemistry, Oct. 10, 1997, pp. 25483-25492, vol. 272, No. 41.

Ruczinski, Ingo et al., "Logic Regression," Journal of Computational and Graphical Statistics, 2003, pp. 475-511, vol. 12, No. 3.

Scanlan, Matthew J. et al., "Molecular cloning of fibroblast activation protein α, a member of the serine protease family selectively expressed in stromal fibroblasts of epithelial cancers," Proceedings of the National Academy of Sciences, Jun. 1994, pp. 5657-5661, vol. 91.

Schneider, Joachim et al., "Fuzzy logic-based tumor-marker profiles improved sensitivity in the diagnosis of lung cancer," International Journal of Clinical Oncology, 2002, pp. 145-151, vol. 7.

Scholefield, J. H. et al., "Serum Ferritin Screening Test for Colorectal Cancer?" Diseases of the Colon & Rectum, 1998, pp. 1029-1032, vol. 41.

Senger, Donald R. et al., Elevated Expression of Secreted Phosphoprotein I (Osteopontin, 2ar) as a Consequence of Neoplastic Transformation, Anticancer Research, 1989, pp. 1291-1300, vol. 9.

Singh, Rajesh P. et al., "Definition of a Specific Interaction Between the Early T Lymphocyte Activation 1 (Eta-1) Protein and Murine Macrophases In Vitro and Its Effect Upon Macrophages In Vivo," Journal of Experimental Medicine, Jun. 1990, pp. 1931-1942, vol. 171.

Soussi, Thierry, "p53 Antibodies in the Sera of Patients with Various Types of Cancer: A Review," Cancer Research, Apr. 1, 2000, pp. 1777-1788, vol. 60.

Sulda, Melanie L. et al., "DPIV/CD26 and FAP in Cancer: A Tale of Contradictions," Advances in Experimental Medicine and Biology, Jan. 2006, pp. 197-206, vol. 575.

(56) References Cited

OTHER PUBLICATIONS

Tan, Eng M. and Zhang, Jianying, "Autoantibodies to tumor-associated antigens: reporters from the immune system," Immunological Reviews, 2008, pp. 328-340, vol. 222.

Tanahashi, Nobuyuki et al., "Molecular properties of the proteasome activator PA28 family proteins and γ-interferon regulation," Genes to Cells, 1997, pp. 195-211, vol. 2.

Tonini, Gian Paolo et al., "Inducible Expression of Calcyclin, a Gene with Strong Homology to S-100 Protein, during Neuroblastoma Cell Differentiation and Its Prevalent Expression in Schwann-like Cell Lines," Cancer Research, Mar. 15, 1991, pp. 1733-1737, vol. 51.

Wagner, Henry Jr., "Postoperative Adjuvant Therapy for Patients With Resected Non-Small Cell Lung Cancer: Still Controversial After all These Years," Chest, 2000, pp. 110S-118S, vol. 117.

Zhang, Jian-Ying et al., "Enhancement of Antibody Detection in Cancer Using Panel of Recombinant Tumor-associated Antigens," Cancer Epidemiology, Biomarkers & Prevention, Feb. 2003, pp. 136-143, vol. 12.

Zimmer, Danna B. et al., "The S100 Protein Family: History, Function, and Expression," Brain Research Bulletin, 1995, pp. 417-429, vol. 37, No. 4.

Zweig, Mark H. and Campbell, Gregory, "Receiver-Operating Characteristic (ROC) Plots: A Fundamental Evaluation Tool in Clinical Medicine," Clinical Chemistry, 1993, pp. 561-577, vol. 39, No. 4.

Olivier, M. et al., "Recent advances in p53 research: an interdisciplinary perspective," Cancer Gene Therapy, 2009, pp. 1-12, vol. 16.

\* cited by examiner

Distribution of DPPIV/seprase values within the cohorts of CRC patients and healthy controls Distribution of DPPIV/seprase values within the cohorts of LC, head and neck- and pancreatic cancer patients and healthy controls

SEQUENCE LISTING

<160> NUMBER OF SEQ ID NOS: 4

<210> SEQ ID NO 1
<211> LENGTH: 760
<212> TYPE: PRT
<213> ORGANISM: Homo sapiens

<400> SEQUENCE: 1

```
Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
            20                  25                  30

Asn Ser Glu Glu Asn Thr Met Arg Ala Leu Thr Leu Lys Asp Ile Leu
        35                  40                  45

Asn Gly Thr Phe Ser Tyr Lys Thr Phe Phe Pro Asn Trp Ile Ser Gly
    50                  55                  60

Gln Glu Tyr Leu His Gln Ser Ala Asp Asn Asn Ile Val Leu Tyr Asn
65                  70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
    130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Met Leu Pro Thr
        195                 200                 205

Lys Tyr Ala Leu Trp Trp Ser Pro Asn Gly Lys Phe Leu Ala Tyr Ala
    210                 215                 220

Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
                245                 250                 255

Ala Lys Asn Pro Val Val Arg Ile Phe Ile Ile Asp Thr Thr Tyr Pro
            260                 265                 270

Ala Tyr Val Gly Pro Gln Glu Val Pro Val Pro Ala Met Ile Ala Ser
        275                 280                 285

Ser Asp Tyr Tyr Phe Ser Trp Leu Thr Trp Val Thr Asp Glu Arg Val
    290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
                325                 330                 335

Glu His Ile Glu Glu Ser Arg Thr Gly Trp Ala Gly Gly Phe Phe Val
            340                 345                 350

Ser Thr Pro Val Phe Ser Tyr Asp Ala Ile Ser Tyr Tyr Lys Ile Phe
        355                 360                 365
```

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
            405                 410                 415

Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
            435                 440                 445

Gln Tyr Tyr Thr Ala Ser Phe Ser Asp Tyr Ala Lys Tyr Tyr Ala Leu
450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
            485                 490                 495

Ala Leu Lys Asn Ile Gln Leu Pro Lys Glu Glu Ile Lys Lys Leu Glu
            500                 505                 510

Val Asp Glu Ile Thr Leu Trp Tyr Lys Met Ile Leu Pro Pro Gln Phe
515                 520                 525

Asp Arg Ser Lys Lys Tyr Pro Leu Leu Ile Gln Val Tyr Gly Gly Pro
530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
            565                 570                 575

Thr Ala Phe Gln Gly Asp Lys Leu Leu Tyr Ala Val Tyr Arg Lys Leu
            580                 585                 590

Gly Val Tyr Glu Val Glu Asp Gln Ile Thr Ala Val Arg Lys Phe Ile
            595                 600                 605

Glu Met Gly Phe Ile Asp Glu Lys Arg Ile Ala Ile Trp Gly Trp Ser
            610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
            645                 650                 655

Ala Ser Val Tyr Thr Glu Arg Phe Met Gly Leu Pro Thr Lys Asp Asp
            660                 665                 670

Asn Leu Glu His Tyr Lys Asn Ser Thr Val Met Ala Arg Ala Glu Tyr
            675                 680                 685

Phe Arg Asn Val Asp Tyr Leu Leu Ile His Gly Thr Ala Asp Asp Asn
690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
            725                 730                 735

Ser Gly Leu Ser Thr Asn His Leu Tyr Thr His Met Thr His Phe Leu
            740                 745                 750

Lys Gln Cys Phe Ser Leu Ser Asp
            755                 760

<210> SEQ ID NO 2
<211> LENGTH: 766
<212> TYPE: PRT

<213> ORGANISM: Homo sapiens

<400> SEQUENCE: 2

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
    370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
    450                 455                 460

Ala Lys Tyr Tyr Gln Leu Arg Cys Ser Gly Pro Gly Leu Pro Leu Tyr
465                 470                 475                 480

Thr Leu His Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
                500                 505                 510

Lys Leu Asp Phe Ile Ile Leu Asn Glu Thr Lys Phe Trp Tyr Gln Met
            515                 520                 525

Ile Leu Pro Pro His Phe Asp Lys Ser Lys Tyr Pro Leu Leu Leu
        530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
                580                 585                 590

Ala Ile Asn Arg Arg Leu Gly Thr Phe Glu Val Glu Asp Gln Ile Glu
            595                 600                 605

Ala Ala Arg Gln Phe Ser Lys Met Gly Phe Val Asp Asn Lys Arg Ile
        610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
                660                 665                 670

Leu Pro Thr Pro Glu Asp Asn Leu Asp His Tyr Arg Asn Ser Thr Val
            675                 680                 685

Met Ser Arg Ala Glu Asn Phe Lys Gln Val Glu Tyr Leu Leu Ile His
        690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
                740                 745                 750

Thr His Met Ser His Phe Ile Lys Gln Cys Phe Ser Leu Pro
        755                 760                 765

<210> SEQ ID NO 3
<211> LENGTH: 738
<212> TYPE: PRT
<213> ORGANISM: Homo sapiens

<400> SEQUENCE: 3

Asn Lys Gly Thr Asp Asp Ala Thr Ala Asp Ser Arg Lys Thr Tyr Thr
1               5                   10                  15

-continued

```
Leu Thr Asp Tyr Leu Lys Asn Thr Tyr Arg Leu Lys Leu Tyr Ser Leu
             20                  25                  30

Arg Trp Ile Ser Asp His Glu Tyr Leu Tyr Lys Gln Glu Asn Asn Ile
             35                  40                  45

Leu Val Phe Asn Ala Glu Tyr Gly Asn Ser Ser Val Phe Leu Glu Asn
 50                  55                  60

Ser Thr Phe Asp Glu Phe Gly His Ser Ile Asn Asp Tyr Ser Ile Ser
 65                  70                  75                  80

Pro Asp Gly Gln Phe Ile Leu Leu Glu Tyr Asn Tyr Val Lys Gln Trp
                 85                  90                  95

Arg His Ser Tyr Thr Ala Ser Tyr Asp Ile Tyr Asp Leu Asn Lys Arg
             100                 105                 110

Gln Leu Ile Thr Glu Glu Arg Ile Pro Asn Asn Thr Gln Trp Val Thr
             115                 120                 125

Trp Ser Pro Val Gly His Lys Leu Ala Tyr Val Trp Asn Asn Asp Ile
130                 135                 140

Tyr Val Lys Ile Glu Pro Asn Leu Pro Ser Tyr Arg Ile Thr Trp Thr
145                 150                 155                 160

Gly Lys Glu Asp Ile Ile Tyr Asn Gly Ile Thr Asp Trp Val Tyr Glu
                 165                 170                 175

Glu Glu Val Phe Ser Ala Tyr Ser Ala Leu Trp Trp Ser Pro Asn Gly
             180                 185                 190

Thr Phe Leu Ala Tyr Ala Gln Phe Asn Asp Thr Glu Val Pro Leu Ile
             195                 200                 205

Glu Tyr Ser Phe Tyr Ser Asp Glu Ser Leu Gln Tyr Pro Lys Thr Val
             210                 215                 220

Arg Val Pro Tyr Pro Lys Ala Gly Ala Val Asn Pro Thr Val Lys Phe
225                 230                 235                 240

Phe Val Val Asn Thr Asp Ser Leu Ser Ser Val Thr Asn Ala Thr Ser
                 245                 250                 255

Ile Gln Ile Thr Ala Pro Ala Ser Met Leu Ile Gly Asp His Tyr Leu
             260                 265                 270

Cys Asp Val Thr Trp Ala Thr Gln Glu Arg Ile Ser Leu Gln Trp Leu
             275                 280                 285

Arg Arg Ile Gln Asn Tyr Ser Val Met Asp Ile Cys Asp Tyr Asp Glu
290                 295                 300

Ser Ser Gly Arg Trp Asn Cys Leu Val Ala Arg Gln His Ile Glu Met
305                 310                 315                 320

Ser Thr Thr Gly Trp Val Gly Arg Phe Arg Pro Ser Glu Pro His Phe
                 325                 330                 335

Thr Leu Asp Gly Asn Ser Phe Tyr Lys Ile Ile Ser Asn Glu Glu Gly
             340                 345                 350

Tyr Arg His Ile Cys Tyr Phe Gln Ile Asp Lys Lys Asp Cys Thr Phe
             355                 360                 365

Ile Thr Lys Gly Thr Trp Glu Val Ile Gly Ile Glu Ala Leu Thr Ser
             370                 375                 380

Asp Tyr Leu Tyr Tyr Ile Ser Asn Glu Tyr Lys Gly Met Pro Gly Gly
385                 390                 395                 400

Arg Asn Leu Tyr Lys Ile Gln Leu Ser Asp Tyr Thr Lys Val Thr Cys
                 405                 410                 415

Leu Ser Cys Glu Leu Asn Pro Glu Arg Cys Gln Tyr Tyr Ser Val Ser
             420                 425                 430
```

Phe Ser Lys Glu Ala Lys Tyr Tyr Gln Leu Arg Cys Ser Gly Pro Gly
            435                 440                 445

Leu Pro Leu Tyr Thr Leu His Ser Ser Val Asn Asp Lys Gly Leu Arg
        450                 455                 460

Val Leu Glu Asp Asn Ser Ala Leu Asp Lys Met Leu Gln Asn Val Gln
465                 470                 475                 480

Met Pro Ser Lys Lys Leu Asp Phe Ile Ile Leu Asn Glu Thr Lys Phe
                485                 490                 495

Trp Tyr Gln Met Ile Leu Pro Pro His Phe Asp Lys Ser Lys Lys Tyr
                500                 505                 510

Pro Leu Leu Leu Asp Val Tyr Ala Gly Pro Cys Ser Gln Lys Ala Asp
            515                 520                 525

Thr Val Phe Arg Leu Asn Trp Ala Thr Tyr Leu Ala Ser Thr Glu Asn
530                 535                 540

Ile Ile Val Ala Ser Phe Asp Gly Arg Gly Ser Gly Tyr Gln Gly Asp
545                 550                 555                 560

Lys Ile Met His Ala Ile Asn Arg Arg Leu Gly Thr Phe Glu Val Glu
                565                 570                 575

Asp Gln Ile Glu Ala Ala Arg Gln Phe Ser Lys Met Gly Phe Val Asp
                580                 585                 590

Asn Lys Arg Ile Ala Ile Trp Gly Trp Ser Tyr Gly Gly Tyr Val Thr
            595                 600                 605

Ser Met Val Leu Gly Ser Gly Ser Gly Val Phe Lys Cys Gly Ile Ala
        610                 615                 620

Val Ala Pro Val Ser Arg Trp Glu Tyr Tyr Asp Ser Val Tyr Thr Glu
625                 630                 635                 640

Arg Tyr Met Gly Leu Pro Thr Pro Glu Asp Asn Leu Asp His Tyr Arg
                645                 650                 655

Asn Ser Thr Val Met Ser Arg Ala Glu Asn Phe Lys Gln Val Glu Tyr
                660                 665                 670

Leu Leu Ile His Gly Thr Ala Asp Asp Asn Val His Phe Gln Gln Ser
            675                 680                 685

Ala Gln Ile Ser Lys Ala Leu Val Asp Val Gly Val Asp Phe Gln Ala
        690                 695                 700

Met Trp Tyr Thr Asp Glu Asp His Gly Ile Ala Ser Ser Thr Ala His
705                 710                 715                 720

Gln His Ile Tyr Thr His Met Ser His Phe Ile Lys Gln Cys Phe Ser
                725                 730                 735

Leu Pro

<210> SEQ ID NO 4
<211> LENGTH: 735
<212> TYPE: PRT
<213> ORGANISM: Homo sapiens

<400> SEQUENCE: 4

Leu Arg Pro Ser Arg Val His Asn Ser Glu Glu Asn Thr Met Arg Ala
1               5                   10                  15

Leu Thr Leu Lys Asp Ile Leu Asn Gly Thr Phe Ser Tyr Lys Thr Phe
            20                  25                  30

Phe Pro Asn Trp Ile Ser Gly Gln Glu Tyr Leu His Gln Ser Ala Asp
        35                  40                  45

Asn Asn Ile Val Leu Tyr Asn Ile Glu Thr Gly Gln Ser Tyr Thr Ile
    50                  55                  60

```
Leu Ser Asn Arg Thr Met Lys Ser Val Asn Ala Ser Asn Tyr Gly Leu
 65                  70                  75                  80

Ser Pro Asp Arg Gln Phe Val Tyr Leu Glu Ser Asp Tyr Ser Lys Leu
                 85                  90                  95

Trp Arg Tyr Ser Tyr Thr Ala Thr Tyr Tyr Ile Tyr Asp Leu Ser Asn
                100                 105                 110

Gly Glu Phe Val Arg Gly Asn Glu Leu Pro Arg Pro Ile Gln Tyr Leu
            115                 120                 125

Cys Trp Ser Pro Val Gly Ser Lys Leu Ala Tyr Val Tyr Gln Asn Asn
        130                 135                 140

Ile Tyr Leu Lys Gln Arg Pro Gly Asp Pro Pro Phe Gln Ile Thr Phe
145                 150                 155                 160

Asn Gly Arg Glu Asn Lys Ile Phe Asn Gly Ile Pro Asp Trp Val Tyr
                165                 170                 175

Glu Glu Glu Met Leu Pro Thr Lys Tyr Ala Leu Trp Trp Ser Pro Asn
                180                 185                 190

Gly Lys Phe Leu Ala Tyr Ala Glu Phe Asn Asp Thr Asp Ile Pro Val
            195                 200                 205

Ile Ala Tyr Ser Tyr Tyr Gly Asp Glu Gln Tyr Pro Arg Thr Ile Asn
210                 215                 220

Ile Pro Tyr Pro Lys Ala Gly Ala Lys Asn Pro Val Val Arg Ile Phe
225                 230                 235                 240

Ile Ile Asp Thr Thr Tyr Pro Ala Tyr Val Gly Pro Gln Glu Val Pro
                245                 250                 255

Val Pro Ala Met Ile Ala Ser Ser Asp Tyr Tyr Phe Ser Trp Leu Thr
            260                 265                 270

Trp Val Thr Asp Glu Arg Val Cys Leu Gln Trp Leu Lys Arg Val Gln
        275                 280                 285

Asn Val Ser Val Leu Ser Ile Cys Asp Phe Arg Glu Asp Trp Gln Thr
        290                 295                 300

Trp Asp Cys Pro Lys Thr Gln Glu His Ile Glu Glu Ser Arg Thr Gly
305                 310                 315                 320

Trp Ala Gly Gly Phe Phe Val Ser Thr Pro Val Phe Ser Tyr Asp Ala
                325                 330                 335

Ile Ser Tyr Tyr Lys Ile Phe Ser Asp Lys Asp Gly Tyr Lys His Ile
                340                 345                 350

His Tyr Ile Lys Asp Thr Val Glu Asn Ala Ile Gln Ile Thr Ser Gly
            355                 360                 365

Lys Trp Glu Ala Ile Asn Ile Phe Arg Val Thr Gln Asp Ser Leu Phe
        370                 375                 380

Tyr Ser Ser Asn Glu Phe Glu Glu Tyr Pro Gly Arg Arg Asn Ile Tyr
385                 390                 395                 400

Arg Ile Ser Ile Gly Ser Tyr Pro Pro Ser Lys Lys Cys Val Thr Cys
                405                 410                 415

His Leu Arg Lys Glu Arg Cys Gln Tyr Tyr Thr Ala Ser Phe Ser Asp
            420                 425                 430

Tyr Ala Lys Tyr Tyr Ala Leu Val Cys Tyr Gly Pro Gly Ile Pro Ile
        435                 440                 445

Ser Thr Leu His Asp Gly Arg Thr Asp Gln Glu Ile Lys Ile Leu Glu
        450                 455                 460

Glu Asn Lys Glu Leu Glu Asn Ala Leu Lys Asn Ile Gln Leu Pro Lys
465                 470                 475                 480

Glu Glu Ile Lys Lys Leu Glu Val Asp Glu Ile Thr Leu Trp Tyr Lys
```

-continued

```
                        485                 490                 495
Met Ile Leu Pro Pro Gln Phe Asp Arg Ser Lys Lys Tyr Pro Leu Leu
            500                 505                 510

Ile Gln Val Tyr Gly Gly Pro Cys Ser Gln Ser Val Arg Ser Val Phe
        515                 520                 525

Ala Val Asn Trp Ile Ser Tyr Leu Ala Ser Lys Glu Gly Met Val Ile
        530                 535                 540

Ala Leu Val Asp Gly Arg Gly Thr Ala Phe Gln Gly Asp Lys Leu Leu
545                 550                 555                 560

Tyr Ala Val Tyr Arg Lys Leu Gly Val Tyr Glu Val Glu Asp Gln Ile
                565                 570                 575

Thr Ala Val Arg Lys Phe Ile Glu Met Gly Phe Ile Asp Glu Lys Arg
            580                 585                 590

Ile Ala Ile Trp Gly Trp Ser Tyr Gly Gly Tyr Val Ser Ser Leu Ala
        595                 600                 605

Leu Ala Ser Gly Thr Gly Leu Phe Lys Cys Gly Ile Ala Val Ala Pro
    610                 615                 620

Val Ser Ser Trp Glu Tyr Tyr Ala Ser Val Tyr Thr Glu Arg Phe Met
625                 630                 635                 640

Gly Leu Pro Thr Lys Asp Asp Asn Leu Glu His Tyr Lys Asn Ser Thr
            645                 650                 655

Val Met Ala Arg Ala Glu Tyr Phe Arg Asn Val Asp Tyr Leu Leu Ile
            660                 665                 670

His Gly Thr Ala Asp Asp Asn Val His Phe Gln Asn Ser Ala Gln Ile
        675                 680                 685

Ala Lys Ala Leu Val Asn Ala Gln Val Asp Phe Gln Ala Met Trp Tyr
    690                 695                 700

Ser Asp Gln Asn His Gly Leu Ser Gly Leu Ser Thr Asn His Leu Tyr
705                 710                 715                 720

Thr His Met Thr His Phe Leu Lys Gln Cys Phe Ser Leu Ser Asp
            725                 730                 735
```

USE OF DPPIV/SEPRASE AS A MARKER FOR CANCER

RELATED APPLICATIONS

This application is a continuation of PCT/EP2010/002544 filed Apr. 26, 2010 and claims priority to EP 09006097.1 filed May 4, 2009.

SEQUENCE LISTING

The instant application contains a Sequence Listing which has been submitted in ASCII format via EFS-Web and is hereby incorporated by reference in its entirety. Said ASCII copy, created on Oct. 6, 2011, is named 26090US.txt, and is 26,150 bytes in size.

FIELD

The present invention relates to a method aiding in the assessment of cancer. It discloses the use of "soluble DPPIV/seprase protein complex" (DPPIV/seprase) as a universal marker of different cancer types. Measurement of DPPIV/seprase can, e.g., be used in the early detection or diagnosis of cancer or in the surveillance of patients who undergo surgery.

BACKGROUND

Cancer remains a major public health challenge despite progress in detection and therapy. Cancer cells are characterized by the production of cancer-associated marker proteins. Cancer-associated proteins are found both in the tissues and in the bodily fluids of an individual who carries cancer cells. Their levels usually are low at the early stages of the carcinogenic progress and increase during the disease's progression and only in rare cases proteins are observed showing a decreased level in the course of disease progression. The sensitive detection of these proteins is an advantageous and promising approach for the diagnosis of cancer, in particular in an early stage diagnosis of cancer. The most prevalent cancer types are breast cancer (BC), lung cancer (LC) and colorectal cancer (CRC).

The most important therapeutic approaches for solid tumors are: a) surgical resection of the tumor, b) chemotherapy, c) radiation therapy, d) treatment with biologicals, like anti-tumor antibodies or anti-angiogenic antibodies and e) a combination of the above methods.

Surgical resection of the tumors is widely accepted as a first line treatment for early stage solid tumors. Most cancers, however, are detected only when they become symptomatic, i.e., when patients already are in a rather late stage of disease progression.

The staging of cancer is the classification of the disease in terms of extent, progression, and severity. It groups cancer patients so that generalizations can be made about prognosis and the choice of therapy.

The different stages of BC or CRC used to be classified according to Dukes' stages A to D. Today, the TNM system is the most widely used classification of the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer), Sobin, L. H., Wittekind, Ch. (eds): TNM Classification of Malignant Tumours, sixth edition, 2002). Once the TNM status is determined the patients are grouped into disease stages that are denoted by Roman numerals ranging form I to IV with IV being the most advanced disease stage. TNM staging and UICC disease stages correspond to each other as shown in the following Table taken from Sobin L. H. and Wittekind (eds.) supra.

Interrelation of TNM Staging and UICC Disease Stages

| UICC disease stage | T staging | N staging | M staging |
|---|---|---|---|
| Stage 0 | $T_{is}$ | N0 | M0 |
| Stage I | T1, T2 | N0 | M0 |
| Stage IIA | T3 | N0 | M0 |
| Stage IIB | T4 | N0 | M0 |
| Stage IIIA | T1, T2 | N1 | M0 |
| Stage IIIB | T3, T4 | N1 | M0 |
| Stage IIIC | Any T | N2 | M0 |
| Stage IV | Any T | Any N | M1 |

What is especially important is that early diagnosis of cancer, e.g., of BC or CRC translates to a much better prognosis. In CRC malignant tumors of the colorectum arise from benign tumors, i.e., from adenoma. Therefore, best prognoses have those patients diagnosed at the adenoma stage. Patients diagnosed as early as in stage Tis, N0, M0 or T1-3; N0; M0, if treated properly have a more than 90% chance of survival 5 years after diagnosis as compared to a 5-years survival rate of only 10% for patients diagnosed when distant metastases are already present.

Current detection methods including imaging methods, such as x-ray or nuclear resonance imaging in theory might at least partially be appropriate for use as a general screening tool. However, they are very costly and not affordable to health care systems for a general and broad use in mass screenings of large numbers of subjects, particularly for subjects without any tumor symptoms.

Thus, it is an object of the present invention to provide a simple and cost-efficient procedure of tumor assessments, e.g., to identify individuals suspect of having cancer. For this purpose, a general tumor marker which is detectable in body fluids, e.g., blood or serum or plasma or a panel of such markers, would be desirable.

A number of serum tumor markers are already in clinical use. For example the soluble 30 kDa fragment of cytoceratin 19 (Cyfra 21-1), carcinoembryogenic antigen (CEA), neuron-specific enolase (NSE), and squamous cell carcinoma antigen (SCC) are the most prominent LC markers. However, none of them meets the criteria for sensitivity and specificity required for a screening tool (Thomas, L., Labor and Diagnose, TH Books Verlagsgesellschaft, Frankfurt/Main, Germany (2000)).

In order to be of clinical utility, a new diagnostic marker as a single marker should be comparable to other markers known in the art, or better. Or, a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

Whole blood, serum or plasma are the most widely used sources of sample in clinical routine. The identification of an early tumor marker that would aid in the reliable cancer detection or provide early prognostic information could lead to a method that would greatly aid in the diagnosis and in the management of this disease. Therefore, an urgent clinical need exists to improve the in vitro assessment of cancer and in particular of LC or CRC. It is especially important to improve the early diagnosis of cancer, e.g., LC or CRC, since for patients diagnosed early on chances of survival are much higher as compared to those diagnosed at a progressed stage of disease.

The clinical utility of biochemical markers in lung cancer has recently been reviewed (Duffy, M. J., Critical Reviews in Clinical Laboratory Sciences 38 (2001) 225-262).

Cyfra 21-1 is currently regarded to be the best of the presently known tumor markers for lung cancer. Even though not organ-specific it is predominantly found in lung tissue. Sensitivity of Cyfra 21-1 for lung cancer is described to be between 46-61% at a specificity of 95% towards other benign lung diseases. Increased serum levels of Cyfra 21-1 are also associated with pronounced benign liver diseases, renal insufficiency and invasive bladder cancer. Cyfra 21-1 testing is recommended for postoperative therapy surveillance.

CEA belongs to the group of carcinofetal antigens, usually produced during embryogenesis. CEA is not organ-specific and predominantly used for monitoring of colorectal cancer. Besides malignancies, also several benign diseases such as cirrhosis, bronchitis, pancreatitis and autoimmune diseases are associated with increased CEA serum levels. At 95% specificity towards benign lung diseases its sensitivity for lung cancer is reported to be 29-44%. A preferred use of CEA is therapy surveillance of lung cancer.

FERR (Ferritin) is a protein containing about 20% iron and is found in the intestines, the liver and the spleen. It is one of the chief forms in which iron is stored in the body. Body iron stores have been reported to increase the risk of colorectal neoplasms. In a study by Scholefield, J. H. et al. (Dis. Colon Rectum 41 (1998) 1029-1032) using samples from 148 patients (50 patients with proven colorectal cancer, 49 patients without colon disease, and patients with adenomas of the colon) serum ferritin was assayed. There were no significant differences in serum ferritin levels among any of the three groups.

OPN (Osteopontin) is a cell-binding sialoprotein specific to bone (Kiefer, M. C. et al., Nucl. Acids Res. 17 (1989) 3306). Osteopontin (Oldberg, A. et al., Proc. Natl. Acad. Sci. USA 83 (1986) 8819-8823; Oldberg, A. et al., J. Biol. Chem. 263 (1988) 19433-19436) also known as transformation-associated secreted phosphoprotein (Senger, D. R. et al., Anticancer Res. 9 (1989) 1291-1299), or Early T-lymphocyte activation-1 (Patarca, R. et al., Proc. Natl. Acad. Sci. USA 88 (1991) 2736-2739), is a secreted glycosylated phosphoprotein expressed by bone (Oldberg et al., J. Biol. Chem. 263 (1986) 19433-19436), activated T-lymphocytes (Patarca, R. et al., J. Exp. Med. 170 (1989) 145-161; Patarca, R. et al., Proc. Natl. Acad. Sci. USA 88 (1991) 2736-2739), macrophages (Singh, R. P. et al., J. Exp. Med. 171 (1990) 1931-1942), smooth muscle cells of the vascular system (Giachelli, C. et al., Biochem. Biophys. Res. Commun. 177 (1991) 867-873), and carcinomas and sarcomas (Senger, D. R. et al., Anticancer Res. 9 (1989) 1291-1299).

Seprase, originally identified as a 170 kDa membrane bound gelatinase is expressed on invadopodia of highly aggressive melanoma LOX cells (Aoyama, A. and Chen, W. T., PNAS 87 (1990) 8296-8300; Mueller, S. C. et al., J. Biol. Chem. 274 (1999) 24947-24952; Monsky, W. L. et al., Cancer Res. 54 (1994) 5702-5710). The active enzyme is a homodimer of two subunits (Pineiro-Sanchez, M. L. et al., J. Biol. Chem. 272 (1997) 7595-7601; Park, J. E. et al., J. Biol. Chem. 274 (1999) 36505-36512). Analysis of the deduced amino acid sequence from a cDNA that encodes the 97 kDa subunit (Goldstein, L. A. et al., Biochem. Biophys. Act. 1361 (1997) 11-19) revealed that it is essentially identical to fibroblast activation protein α (FAPα) (Scanlan, M. J. et al., PNAS 91 (1994) 5657-5661), which is expressed on reactive stromal fibroblasts of epithelial cancers and healing wounds (Garin-Chesa, P. et al., PNAS 87 (1990) 7235-7239).

NNMT (nicotinamide N-methyltransferase; Swiss-PROT: P40261) has an apparent molecular weight of 29.6 kDa and an isoelectric point of 5.56. NNMT catalyzes the N-methylation of nicotinamide and other pyridines. This activity is important for biotransformation of many drugs and xenobiotic compounds. The protein has been reported to be predominantly expressed in liver and is located in the cytoplasm. NNMT has been cloned from cDNA from human liver and contained a 792-nucleotide open reading frame that encoded a 264-amino acid protein with a calculated molecular mass of 29.6 kDa (Aksoy, S. et al., J. Biol. Chem. 269 (1994) 14835-14840). Little is known in the literature about a potential role of the enzyme in human cancer. In one paper, increased hepatic NNMT enzymatic activity was reported as a marker for cancer cachexia in mice (Okamura, A. et al., Jpn. J. Cancer Res. 89 (1998) 649-656). In a recent report, down-regulation of the NNMT gene in response to radiation in radiation sensitive cell lines was demonstrated (Kassem, H. S. et al., Int. J. Cancer 101 (2002) 454-460). It has recently been found (WO 2004/057336) that NNMT will be of interest in the assessment of CRC.

With respect to marker profiles and aiming at improved diagnosis of lung cancer, a method was published (Schneider, J. et al., Int. J. Clin. Oncol. 7 (2002) 145-151) using fuzzy logic based classification algorithms to combine serum levels of Cyfra 21-1, NSE and C-reactive protein (CRP) which is a general inflammation marker. The authors report a sensitivity of 92% at a specificity of 95%. However in this study, for example the sensitivity of Cyfra 21-1 as a single tumor marker is reported to be at 72% at a specificity of 95%, which is significantly higher than in many other reported studies. Duffy, M. J., in Critical Reviews in Clinical Laboratory Sciences 38 (2001) 225-262 report a sensitivity of between 46% and 61%. This unusual high performance achieved by Schneider et al., raises some doubts and might be due to several facts. Firstly, the collective of control patients seems to be younger than the patients collective, i.e. the groups are not well age-matched, and the patient collective comprises many late stages. Secondly and even more critical, the performance of the algorithm is checked on the samples of the training set which were used for the determination of the fuzzy logic qualifiers. Hence, these qualifiers are strictly speaking "tailor-made" for this set and not applied to an independent validation set. Under normal circumstances, it has to be expected that the same algorithm applied to a larger, independent, and well balanced validation set will lead to a significantly reduced overall performance. NSE is a tumor marker for SCLC. Generally, increased NSE serum levels are found in association with neuroectodermal and neuroendocrine tumors. Increased serum levels are also found in patients with benign lung diseases and cerebral diseases, such as meningitis or other inflammatory diseases of the brain, and traumatic injuries to the head. While the sensitivity for SCLC at 95% specificity is reported to be 60-87%, the performance of NSE testing for NSCLC is poor (sensitivity of 7-25%). NSE is recommended for therapy surveillance of SCLC.

PSE3 gene was originally isolated 1990 and the corresponding protein was called Ki. Patients with systemic lupus erythematosus (SLE) produce autoantibodies against a number of nuclear antigens, Ki amongst others. Nikaido et al. (Nikaido, T. et al., Clin. Exp. Immunol. 79 (1990) 209-214) isolated the corresponding cDNA by using a bovine cDNA as a probe and screening a cDNA library of a SLE patient. Later on, it was found that recombinant Ki activates the proteasome, and the protein was identified as PSE3 (Realini, C. et al., J. Biol. Chem. 272 (1997) 25483-25492; Tanahashi, N. et al., Genes to Cells 2 (1997) 195-211). Tanahashi, N. et al., supra, also describe an antibody to P28gamma, i.e., to PSE3. Miyagi, T. et al. (Journal of Gastroenterology and Hepatology 18 (2003) 32-40) report that the expression of proteasome subunits and of human leukocyte antigens class I are impaired in human colon cancer cells. PSE3 is abnormally high expressed in thyroid cancer, especially in its growth-accelerated cells, as estimated by immunohistochemical staining and Western Blot (Okamura, T. et al., J. Clin. Endocrin. Metab. 88 (2003) 1374-1383).

S100A12 is also called CAAF1; CAGC; calcium binding protein in amniotic fluid; calgranulin related protein; CGRP; calcium binding protein in amniotic fluid 1; Calgranulin C; ENRAGE (extracellular newly identified RAGE binding protein); neutrophil S100 protein; S100 calcium binding protein A12. The protein encoded by this gene is a member of the S100 family of proteins containing 2 EF-hand calcium-binding motifs. S100 proteins are localized in the cytoplasm and/or nucleus of a wide range of cells, and involved in the regulation of a number of cellular processes such as cell cycle progression and differentiation. S100 genes include at least 13 members which are located as a cluster on chromosome 1q21. This protein is proposed to be involved in specific calcium-dependent signal transduction pathways and its regulatory effect on cytoskeletal components may modulate various neutrophil activities.

CYBP (S100A6) is a calcium-binding protein that belongs to the family of S100 proteins (reviewed in Zimmer, D. B. et al., Brain Res. Bull. 37 (1995) 417-429 and Heizmann, C. W. et al., Biometals 11 (1998) 383-397). Its gene was discovered on the basis of its cell cycle-dependent expression (Calabretta, B. et al., J. Biol. Chem. 261 (1986) 12628-12632). This gene is expressed at its maximal level during the transition between G0 to S phase of the cell cycle, but its expression is deregulated in acute myeloid leukemia (Calabretta, B. et al., Proc. Natl. Acad. Sci. U.S.A. 83 (1986) 1495-1498). The protein was first purified and characterized from Ehrlich ascites tumor (EAT)1 cells (Kuznicki, J. et al., Biochem. J. 247 (1987) 663-667, and Kuznicki, J. et al., Biochem. J. 263 (1989) 951-956). Later calcyclin was found to be expressed at high levels in fibroblasts and epithelial cells, in cells with high proliferating activity, and those undergoing differentiation (Leonard, D. G. et al., Mol. Cell. Biol. 7 (1987) 3156-3167; Guo, X. J. et al., Cell Growth Differ. 1 (1990) 333-338; Tonini, G. P. et al., Cancer Res. 51 (1991) 1733-1737; Kuznicki, J. et al., Exp. Cell Res. 200 (1992) 425-430).

ASC, the "apoptosis-associated speck-like protein containing a caspase-associated recruitment domain", is also known as "target of methylation-induced silencing 1" (TMS1) (Swiss-PROT: Q9ULZ3). Caspase-associated recruitment domains (CARDs) mediate the interaction between adaptor proteins such as APAF1 (apoptotic protease activating factor 1) and the pro-form of caspases (e.g., CASP 9) participating in apoptosis. ASC is a member of the CARD-containing adaptor protein family.

NSE: The glycolytic enzyme enolase occurs in a variety of dimeric isoforms comprising three immunologically different subunits termed α, β, and γ. The enolase isoforms αγ and γγ, which are referred to as neuron-specific enolase (NSE) or γ-enolase, are primarily detectable in high concentrations in neurons and neuro-endocrine cells as well as in tumors originating from them (Lamerz R., NSE (Neuronen-spezifische Enolase), γ-Enolase, In: Thomas L (ed) Clinical Laboratory Diagnosis, TH-Books, Frankfurt, 1st English Edition 1998: 979-981, 5. deutsche Auflage 1998: 1000-1003). NSE is described as the marker of first choice in the monitoring of small cell bronchial carcinoma, (Lamerz R., NSE (Neuronen-spezifische Enolase), γ-Enolase, In: Thomas L (ed) Clinical Laboratory Diagnosis, TH-Books, Frankfurt, 1st English Edition 1998: 979-981, 5. deutsche Auflage 1998:1000-1003). Elevated NSE concentrations are found in 60-81% of cases of small cell bronchial carcinoma.

CA 19-9 (carbohydrate antigen 19-9), a sialylated Lewis (a) antigen) on a glycolipid is a tumor marker for gastrointestinal cancers. It occurs in fetal gastric, intestinal and pancreatic epithelia. Low concentrations can also be found in adult tissue in the liver, lungs, and pancreas. There is no correlation between tumor mass and the CA 19-9 assay values Therefore the determination of CA 19-9 cannot be used for the early detection of pancreatic carcinoma. As the mucin is excreted exclusively via the liver, even slight cholestasis can lead to clearly elevated CA 19-9 serum levels in some cases. The marker is mainly used as an aid in the monitoring of disease status in those patients having confirmed pancreatic cancer (sensitivity 70-87%). 3-7% of the population have the Lewis a-negative/b-negative blood group configuration and are unable to express the mucin with the reactive determinant CA 19-9. This must be taken into account when interpreting the findings.

CA 125 is found in a high percentage of non-mucinous ovarian tumors of epithelial origin and can be detected in serum. Ovarian carcinoma accounts for about 20% of gynecological tumors. Although the highest CA 125 values occur in patients suffering from ovarian carcinoma, clearly elevated values are also observed in malignancies of the endometrium, breast, gastrointestinal tract, and various other malignancies. Increased values are sometimes found in various benign gynecological diseases such as ovarian cysts, ovarian metaplasia, endometriosis, uterus myomatosus or cervicitis. Slight elevations of this marker may also occur in early pregnancy and in various benign diseases (e.g., acute and chronic pancreatitis, benign gastrointestinal diseases, renal insufficiency, autoimmune diseases and others). Markedly elevated levels have been found in benign liver diseases such as cirrhosis and hepatitis. Extreme elevations can occur in any kind of ascites due to malignant and benign diseases. Although CA 125 is a relatively unspecific marker, it is today the most important tumor marker for monitoring the therapy and progress of patients with serous ovarian carcinoma. A sensitivity of 69-79% is reported for 82-93% specificity.

p53 (TP53, cellular tumor antigen p53, tumor suppressor p53 or phosphoprotein p53) is a transcription factor inducing cell growth arrest or apoptosis (Appella, E. et al., Pathol. Biol. 48 (2000) 227-245). p53 acts as a tumor suppressor in many tumor types and inactivating mutations in its gene are the most common genetic events promoting cancer development in humans (reviewed in Olivier, M. and Petitjean, A., Cancer Gene Ther. 16 (2009) 1-12; Petitjean, A. et al., Oncogene 26 (2007) 2157-2165). p53 mutation is observed in 40-50% of colorectal carcinomas, and is associated with carcinoma aggressiveness (Soussi, T., Cancer Res. 60 (2000) 1777-1788). Mutations in p53 gene lead not only to the disruption of the protein function, but also to the expression of tumor-associated antigens (TAA) and initiation of the auto-immune response and generation of specific anti-p53 autoantibodies in sera of cancer patients (Zhang, J. Y. et al., Cancer Epidemiology, Biomarkers & Prevention 12 (2003) 136-143; Soussi, T., Cancer Res. 60 (2000) 1777-1788). Detection of anti-p53 autoantibodies in human sera is an emerging tool for the diagnosis and management of cancer. Dependent of the cancer type, the frequency of anti-p53 autoantibodies in sera range from 17.8% (CRC) to 16.1% (LC) and 7.8% (Breast Cancer) (Tan, E. M., Immunological Reviews 222 (2008) 328-340; Zhang, J. Y. et al., Cancer Epidemiology, Biomarkers & Prevention 12 (2003) 136-143).

It was the object of the present invention to investigate whether a biochemical marker can be identified which may be used in assessing cancer disease. In particular, the inventors of the present invention investigated whether a biochemical marker could be identified for the assessment of different cancer types, such as lung, breast, colon, prostate and kidney cancer in body fluids. In a very preferred aspect of the present invention, the identification of a biochemical marker for the assessment of lung cancer (LC) or colorectal cancer (CRC) was investigated.

Surprisingly, it has been found that use of DPPIV/seprase can at least partially overcome some of the problems of the markers presently known in the state of the art.

SUMMARY

The present invention relates to a method for assessing cancer in vitro comprising measuring in a liquid sample the concentration of a) soluble dipeptidyl peptidase IV/seprase protein complex (DPPIV/seprase), b) optionally one or more other marker of cancer, and c) using the measurement result of step (a) and optionally of step (b) in the assessment of cancer, wherein a decreased concentration of DPPIV/seprase is indicative for cancer.

Further the present invention relates to the use of DPPIV/seprase in the assessment of cancer.

Further the present invention relates to the use of a combination of antibodies directed against either soluble DPPIV or soluble seprase in the assessment of cancer, wherein a decreased concentration of a DPPIV/seprase is indicative for cancer.

Further the present invention discloses the use of a marker panel comprising DPPIV/seprase and optionally one or more other marker for cancer in the assessment of cancer, wherein a decreased concentration of a DPPIV/seprase is indicative for cancer.

Further the present invention relates to a kit for performing the method for assessing cancer in vitro comprising measuring in a sample the concentration of (a) DPPIV/seprase, (b) optionally one or more other marker of cancer, and (c) using the measurement result of step (a) and optionally of step (b) in the assessment of cancer, wherein a decreased concentration of a DPPIV/seprase is indicative for cancer, comprising the reagents required to specifically measure DPPIV/seprase, and optionally the reagents required to specifically measure one or more other marker of cancer.

DESCRIPTION OF THE SEQUENCES

Figure 1:
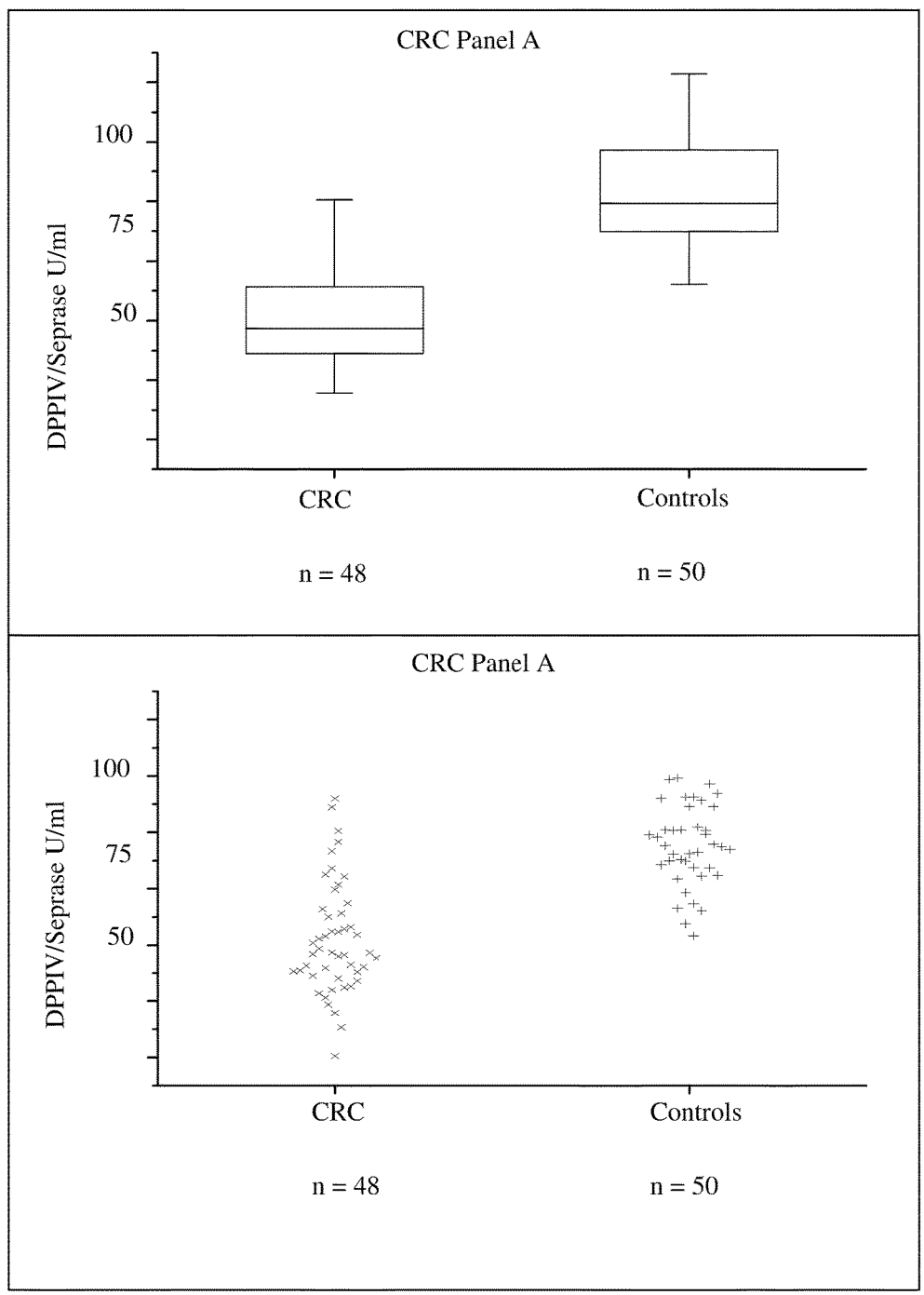
FIG. 1 shows the distribution of serum DPPIV/seprase concentration values in colorectal cancer (CRC) patients and healthy control patients.

SEQ ID NO: 1 shows the amino acid sequence of the human seprase protein (isoform 1); SwissProt database accession number Q12884.

SEQ ID NO: 2 shows the amino acid sequence of the human DPPIV protein; SwissProt database accession number P27487.

SEQ ID NO: 3 shows the amino acid sequence of the soluble human DPPIV protein; position 29 to 766 of Swissprot database accession number P27487.

SEQ ID NO: 4 shows the amino acid sequence of the soluble human seprase protein; position 26 to 760 of Swissprot database accession number Q12884.

DETAILED DESCRIPTION

In a preferred embodiment the present invention relates to a method for assessing cancer in vitro comprising measuring in a sample the concentration of DPPIV/seprase and using the measurement results, particularly the concentration determined in the assessment of cancer.

In another preferred embodiment the present invention relates to a method for assessing cancer in vitro comprising measuring in a liquid sample the concentration of (a) DPPIV/seprase, (b) optionally one or more other marker of cancer, and (c) using the measurement result of step (a) and optionally of step (b) in the assessment of cancer, wherein a decreased concentration of DPPIV/seprase is indicative for cancer.

Surprisingly, it has been found that a decreased concentration of DPPIV/seprase in the test sample is associated with the occurrence of cancer. It could be shown that DPPIV/seprase is a marker which is not specific for a single type of cancer, but a marker for different types of cancer, i.e., a general tumor marker. Since DPPIV/seprase appears to be rather specific for tumorigenic processes, the novel tumor marker DPPIV/seprase has great potential to be of clinical utility with various classes of tumor types.

Surprisingly, it was found in the present invention that a determination of the concentration of DPPIV/seprase in a sample and/or body fluid, allows the assessment of cancer, e.g., of lung, colon, head and neck, pancreas, stomach, bile duct, esophagus, kidney, cervix, ovary, breast, bladder, endometrium or prostate cancer. Even more surprisingly, it was found that a decreased concentration of DPPIV/seprase or fragments thereof in a sample and/or body fluid compared to normal controls is indicative for the risk or occurrence of cancer.

The present invention relates to a method for assessing cancer in vitro comprising measuring in a sample the concentration of DPPIV/seprase by an immunological detection method and using the measurement result, particularly the concentration determined in the assessment of cancer.

The method of the present invention is suitable for the assessment of many different types of cancer. Decreased concentrations of DPPIV/seprase in a sample as compared to normal controls have been found for example in specific cancer types like lung, colon, head and neck, pancreas, stomach, bile duct, esophagus, kidney, cervix, ovary, breast, bladder, endometrium or prostate cancer, respectively.

According to a preferred embodiment of the invention, the concentration of DPPIV/seprase is measured in a sample in order to assess specific cancer types, such as lung, colon, head and neck, pancreas, stomach, bile duct, esophagus, kidney, cervix, ovary, breast, bladder, endometrium or prostate cancer in vitro.

According to another preferred embodiment of the invention, the concentration of DPPIV/seprase is measured in a sample in order to assess cancer, such as lung, colon, head and neck and pancreas cancer in vitro.

According to another preferred embodiment of the invention, the concentration of DPPIV/seprase is measured in a sample in order to assess cancer, such as lung cancer (LC) or colorectal cancer (CRC) in vitro.

According to another preferred embodiment of the invention, the concentration of DPPIV/seprase is measured in a sample in order to assess cancer, such as LC in vitro.

According to another preferred embodiment of the invention, the concentration of DPPIV/seprase is measured in a sample in order to assess cancer, such as CRC in vitro.

One embodiment of the present invention refers to the mass screening of a population to distinguish between individuals which are probably free from cancer and individuals which might be classified as "suspect" cases. The latter group of individuals could then be subjected to further diagnostic procedures, e.g., by imaging methods or other suitable means.

A further embodiment of the present invention refers to an improvement of tumor marker panels which are suitable for the diagnosis of cancer in general or tumor marker panels which are suitable for the diagnosis of a specific tumor type, e.g., lung cancer or colon cancer.

The present invention is also directed to a method for assessing cancer in vitro by biochemical marker, comprising measuring in a sample the concentration of DPPIV/seprase and of one or more other markers specific for cancer, and using the measurement results, particularly concentrations, determined in the assessment of cancer. Preferred markers for use in combination with DPPIV/seprase are, on the one hand, markers which are general tumor markers (i.e., markers which are not specific for a single tumor type) or, on the other hand, specific tumor markers (markers which are specific for a single tumor type). Preferred markers, e.g., for the assessment of cancer, such as lung cancer or colon cancer, are Cyfra 21-1, CEA, FERR, OPN, anti-p53 autoantibodies, seprase, NNMT, PSE3, S100A12, CYBP, ASC, NSE, CA19-9 and CA125. These markers may be used individually each or in any combination together with DPPIV/seprase.

The present invention is also directed to a method for assessing cancer, such as lung cancer or colon cancer in vitro by biochemical markers, comprising measuring in a sample the concentration of DPPIV/seprase and of one or more other cancer markers, e.g., one or more other markers of lung or colon cancer and using the measurement results, particularly concentrations determined in the assessment of cancer. It is preferred that the one or more other marker is selected from the group consisting of Cyfra 21-1, CEA, FERR, OPN, anti-p53 autoantibodies, seprase, NNMT, PSE3, S100A12, CYBP, ASC, NSE, CA19-9 and CA125.

The present invention also relates to the use of a marker panel comprising at least DPPIV/seprase and one or more other marker(s) selected from the group consisting of CYBP, NNMT, PSE3, ASC, OPN, seprase, S100A12, NSE, CEA and Cyfra 21-1, in the assessment of LC, and more particularly NSCLC.

The present invention also relates to the use of a marker panel comprising at least DPPIV/seprase and one or more other marker(s) selected from the group consisting of FERR, OPN, anti-p53 autoantibodies, seprase, CEA and Cyfra 21-1, in the assessment of colon cancer, and more particularly CRC.

The present invention also relates to the use of DPPIV/seprase in the assessment of cancer, wherein a decreased concentration of DPPIV/seprase is indicative for cancer.

The present invention also relates to the use of DPPIV/seprase in the assessment of several specific types of cancer, particularly lung, colon, head and neck, pancreas, esophagus, stomach, bile duct, kidney, cervix, ovary, breast, bladder, endometrium or prostate cancer.

The present invention also relates to the use of DPPIV/seprase in the assessment of several specific types of cancer, particularly lung, colon, head and neck or pancreas cancer.

The present invention also relates to the use of a combination of specific binding agents directed against either soluble DPPIV, soluble seprase or DPPIV/seprase in the assessment of cancer, wherein a decreased concentration of DPPIV/seprase is indicative for cancer.

Preferably DPPIV/seprase is detected in a sandwich-type immunoassay format (sandwich immunoassay).

The present invention is also directed to a sandwich immunoassay format with a first specific binding agent that binds to the soluble DPPIV as part of the DPPIV/seprase and a second specific binding agent that binds to the soluble seprase as part of the DPPIV/seprase, respectively.

The present invention is also directed to a sandwich immunoassay format with a specific binding agent that binds to the soluble DPPIV/seprase protein complex but not to soluble DPPIV or soluble seprase, respectively.

The present invention is also directed to a sandwich immunoassay format with binding agents characterized in that either a first specific binding agent or a second specific binding agent is used as a capture binding agent and either said second specific binding agent or said first specific binding agent is used as a detection binding agent, respectively.

The present invention also provides a kit for performing the method according to the present invention comprising at least the reagents required to specifically measure DPPIV/seprase and one or more other marker of cancer.

The present invention also provides a kit for performing the method according to the present invention comprising at least the reagents required to specifically measure DPPIV/seprase and one or more markers of cancer, e.g., markers of lung, colon, head and neck, pancreas, esophagus, stomach, bile duct, kidney, cervix, ovary, breast, bladder, endometrium or prostate cancer, as described above, wherein the other markers may be each used individually or in any combination thereof.

The present invention also provides a kit for performing the method according to the present invention comprising at least the reagents required to specifically measure DPPIV/seprase and one or more other marker(s) selected from the group consisting of Cyfra 21-1, CEA, FERR, OPN, anti-p53 autoantibodies, seprase, NNMT, PSE3, S100A12, CYBP, ASC, NSE, CA19-9 and CA125, and optionally auxiliary reagents for performing the measurement.

The present invention also provides a bio-chip array for performing the method according to the present invention to specifically measure DPPIV/seprase and one or more other marker selected from the group consisting of Cyfra 21-1, CEA, FERR, OPN, anti-p53 autoantibodies, seprase, NNMT, PSE3, S100A12, CYBP, ASC, NSE, CA19-9 and CA125, and optionally auxiliary reagents for performing the measurement.

The present invention also provides a bio-chip array for performing the method according to the present invention to specifically measure DPPIV/seprase and one or more other marker selected from the group consisting of CYBP, NNMT, PSE3, ASC, OPN, seprase, S100A12, NSE, CEA and Cyfra 21-1, in the assessment of LC, and more particularly NSCLC.

The present invention also provides a bio-chip array for performing the method according to the present invention to specifically measure DPPIV/seprase and one or more other marker selected from the group consisting of FERR, OPN, anti-p53 autoantibodies, seprase, CEA and Cyfra 21-1, in the assessment of colon cancer, and more particularly CRC.

The term "measurement" preferably comprises a semi-qualitative or a quantitative measurement of DPPIV/seprase in a sample. In a preferred embodiment the measurement is a semi-quantitative measurement, i.e., it is determined whether the concentration DPPIV/seprase is above or below a cut-off value. As the skilled artisan will appreciate, in a Yes—(presence) or No—(absence) assay, the assay sensitivity is usually set to match the cut-off value. A cut-off value can for example be determined from the testing of a group of healthy individuals. Preferably the cut-off is set to result in a specificity of 90%, also preferred the cut-off is set to result in a specificity of 95%, or also preferred the cut-off is set to result in a specificity of 98%. Presence or a value below the cut-off value can for example be indicative for the presence of cancer. In particular, presence or a value below the cut-off value can for example be indicative for the presence of lung, colon, esophagus, head and neck, stomach, bile duct, pancreas, kidney, cervix, ovary, breast, bladder, endometrium or prostate cancer. In a further preferred embodiment the measurement of DPPIV/seprase is a quantitative measurement. In further embodiment the concentration of DPPIV/seprase is correlated to an underlying diagnostic question like e.g., stage of disease, disease progression, or response to therapy.

In certain other preferred embodiments, e.g., in monitoring of therapy or follow-up, the cut-off is set to result in a sensitivity of 90%, also preferred the cut-off is set to result in a sensitivity of 95%, or also preferred the cut-off is set to result in a sensitivity of 98%.

A value above the cut-off value can for example be indicative for the absence of cancer. In particular a value above the cut-off value can for example be indicative for the absence of breast, colorectal and/or ovarian cancer.

In a further preferred embodiment the measurement of DPPIV/seprase is a quantitative measurement. In further embodiments the concentration of soluble DPPIV/seprase protein complex is correlated to an underlying diagnostic question like e.g., stage of disease, disease progression, or response to therapy.

Human membrane bound seprase, also known as fibroblast activation protein (FAP), is as a 170 kDa glycoprotein having gelatinase and dipeptidyl peptidase activity consisting of two identical monomeric seprase units (Pineiro-Sanchez, M. L. et al., J. Biol. Chem. 272 (1997) 7595-7601; Park, J. E. et al., J. Biol. Chem. 274 (1999) 36505-36512). The monomer of the human seprase protein comprises 760 amino acids shown in SEQ ID NO: 1 (Swissprot database Accession No. Q12884).

A shorter form of human seprase protein is known to a person skilled in the art as soluble seprase or circulating antiplasmin-cleaving enzyme (APCE) (Lee, K. N. et al., Blood 103 (2004) 3783-3788; Lee, K. N. et al., Blood 107 (2006) 1397-1404). Human soluble seprase amino acid sequence is shown in SEQ ID NO: 4 and comprises the amino acid positions 26-760 from Swissprot database Accession number Q12884. Human seprase is predicted to have its first 4 N-terminal residues within the fibroblast cytoplasm, followed by a 21-residue transmembrane domain and then a 734 residue extracellular C-terminal catalytic domain (Goldstein, L. A. et al., Biochim Biophys Acta. 1361 (1997) 11-19; Scanlan, M. J. et al., Proc Natl Acad Sci USA 91 (1994) 5657-5661). The dimer of soluble seprase is a 160 kDa glycoprotein consisting of two identical monomeric soluble seprase protein units. It has been shown that soluble seprase can be further processed on the N-terminus to 70 kDa or 50 kDa fragments (Chen, D. et al., Cancer Res. 66 (2006) 9977-9985).

Piñeiro-Sanchez et al. (supra) found that an increased expression of seprase correlates with the invasive phenotype of human melanoma and carcinoma cells. Henry, L. R. et al., Clin. Cancer Res. 13 (2007) 1736-1741 describe that human colon tumor patients having high levels of stromal seprase are more likely to have aggressive disease progression and potential development of metastases or recurrence.

Human dipeptidyl peptidase IV (DPPIV), which is also known as CD26, is a 110 kDa cell surface molecule. The amino acid sequence of human DPPIV protein comprises 766 amino acids and is shown in SEQ ID NO: 2 (Swissprot database Accession No. P27487). It contains intrinsic dipeptidyl peptidase IV activity which selectively removes N-terminal dipeptide from peptides with proline or alanine in the third amino acid position. It interacts with various extracellular molecules and is also involved in intracellular signal transduction cascades. The multifunctional activities of human DPPIV are dependent on cell type and intracellular or extracellular conditions that influence its role as a proteolytic enzyme, cell surface receptor, co-stimulatory interacting protein and signal transduction mediator. Human DPPIV has a short cytoplasmatic domain from amino acid position 1 to 6, a transmembrane region from amino acid position 7 to 28, and an extracellular domain from amino acid position 29 to 766 with intrinsic dipeptidyl peptidase IV (DPPIV) activity.

Human soluble dipeptidyl peptidase IV (soluble DPPIV) amino acid sequence is shown in SEQ ID NO: 3, and comprises the amino acid positions 29 to 766 from Swissprot database Accession number P27487. The dimer of soluble DPPIV is a 170 kDa glycoprotein consisting of two identical monomeric soluble DPPIV units.

Membrane bound human DPPIV/seprase protein complex is formed of a 220 kDa DPPIV homodimer and a 170 kDa seprase homodimer having an molecular weight of 410 kDa. Under certain conditions this complex may form a double complex having a molecular weight of 820 kDa. This membrane bound DPPIV/seprase protein complexes have been reported by Ghersi, G. et al., J. Biol. Chem. 277 (2002) 29231-29241; Ghersi, G. et al., Adv. Exp. Med. Biol. 524 (2003) 87-94, and Ghersi, G. et al., Cancer Res. 66 (2006) 4652-4661 in human endothelial cells.

According to the present invention, the term "soluble DPPIV/seprase protein complex" (DPPIV/seprase) refers to the soluble complex formed of a soluble DPPIV homodimer (170 kDa) and a soluble seprase homodimer (160 kDa) with a molecular weight of 330 kDa. Under certain conditions this complex may form a double complex having a molecular weight of 660 kDa.

Hence, none of the above documents of the art suggests that a decreased concentration of the DPPIV/seprase in body fluids would be indicative for cancer.

As obvious to the skilled artisan, the present invention shall not be construed to be limited to the complex formed of soluble DPPIV of SEQ ID NO: 3 and soluble seprase of SEQ ID NO: 4. DPPIV/seprase also may comprise physiological or artificial fragments of DPPIV or seprase, secondary modifications of DPPIV or seprase, as well as allelic variants of DPPIV or seprase. Therefore, DPPIV as well as fragments, modifications and variants of DPPIV being bound to seprase or to fragments, modifications and variants thereof are also encompassed by the present invention.

DPPIV/seprase is detected in appropriate samples. Preferred samples are body fluids, such as blood, plasma, serum, sputum, epithelial lining fluid (ELF; preferred in the case of suspected LC), bronchio alveolar lavage (BAL; preferred in the case of suspected LC) etc. Preferably, the sample is derived from a human subject, e.g., a tumor patient or a person in risk of a tumor or a person suspected of having a tumor. Also preferred DPPIV/seprase is detected in a serum or plasma sample.

All these detection techniques may also be employed in the format of microarrays, protein-arrays, antibody microarrays, tissue microarrays, electronic biochip or protein-chip based technologies (see Schena M., Microarray Biochip Technology, Eaton Publishing, Natick, Mass., 2000).

As used herein, each of the following terms has the meaning associated with it in this section.

The articles "a" and "an" are used herein to refer to one or to more than one (i.e., to at least one) of the grammatical object of the article. By way of example, "a marker" means one marker or more than one marker. The term "at least" is used to indicate that optionally one or more further objects may be present. By way of example, a marker panel comprising at least (the markers) DPPIV/seprase and Cyfra 21-1 may optionally comprise one or more other marker.

The expression "one or more" denotes 1 to 50, preferably 1 to 20 also preferred 2, 3, 4, 5, 6, 7, 8, 9, 10, 12, or 15.

The terms "bio-chip", "polymer-chip" or "protein-chip" are used interchangeably and refer to a collection of a large number of probes, markers or biochemical markers arranged on a shared substrate which could be a portion of a silicon wafer, a nylon strip, a plastic strip, or a glass slide.

An "array," "macroarray" or "microarray" is an intentionally created collection of substances, such as molecules, markers, openings, microcoils, detectors and/or sensors, attached to or fabricated on a substrate or solid surface, such as glass, plastic, silicon chip or other material forming an array. The arrays can be used to measure the levels of large numbers, e.g., tens, thousands or millions, of reactions or combinations simultaneously. An array may also contain a small number of substances, e.g., one, a few or a dozen. The substances in the array can be identical or different from each other. The array can assume a variety of formats, e.g., libraries of soluble molecules, libraries of immobilized molecules, libraries of immobilized antibodies, libraries of compounds tethered to resin beads, silica chips, or other solid supports. The array could either be a macroarray or a microarray, depending on the size of the pads on the array.

A macroarray generally contains pad sizes of about 300 microns or larger and can be easily imaged by gel and blot scanners. A microarray would generally contain pad sizes of less than 300 microns.

A "solid support" is insoluble, functionalized, polymeric material to which library members or reagents may be attached or covalently bound (often via a linker) to be immobilized or allowing them to be readily separated (by filtration, centrifugation, washing etc.) from excess reagents, soluble reaction by-products, or solvents.

The term "marker" or "biochemical marker" as used herein refers to a molecule to be used as a target for analyzing a patient's test sample. Examples of such molecular targets are proteins or polypeptides. Proteins or polypeptides used as a marker in the present invention are contemplated to include naturally occurring variants of said protein as well as fragments of said protein or said variant, in particular, immunologically detectable fragments. Immunologically detectable fragments preferably comprise at least 6, 7, 8, 10, 12, 15 or 20 contiguous amino acids of said marker polypeptide. One of skill in the art would recognize that proteins which are released by cells or present in the extracellular matrix may be damaged, e.g., during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but may differ in their isoelectric point (=PI) or molecular weight (=MW), or both e.g., as a result of alternative mRNA, pre-mRNA processing or protein processing. The amino acid sequence of a variant is to 95% or more identical to the corresponding marker sequence. In addition, or in the alternative a marker polypeptide or a variant thereof may carry a post-translational modification. Preferred posttranslational modifications are glycosylation, acylation, and/or phosphorylation.

A specific binding agent is, e.g., a receptor for DPPIV/seprase, a lectin binding to DPPIV/seprase or an antibody reactive with the DPPIV/seprase. A specific binding agent has at least an affinity of $10^7$ l/mol for its corresponding target molecule. The specific binding agent preferably has an affinity of $10^8$ l/mol or also preferred of $10^9$ l/mol for its target molecule.

A pair of specific binding agents preferably comprises a first antibody reactive with soluble DPPIV and a second antibody reactive with soluble seprase such that the pair of antibodies is capable of forming a complex with the DPPIV/seprase.

Furthermore, a specific binding agent preferably is an antibody specifically reactive with DPPIV/seprase but not soluble DPPIV or soluble seprase alone.

Also encompassed by the present invention is a specific binding agent directed against unbound soluble DPPIV, whereby the specific binding agent preferably is an antibody reactive with an epitope of soluble DPPIV which is masked when soluble DPPIV is bound to soluble seprase. Also encompassed by the present invention is a specific binding agent directed against unbound soluble seprase, whereby the specific binding agent preferably is an antibody reactive with an epitope of soluble seprase which is masked when soluble seprase is bound to soluble DPPIV.

The term antibody refers to a polyclonal antibody, a monoclonal antibody, antigen binding fragments of such antibodies, single chain antibodies as well as to genetic constructs comprising the binding domain of an antibody.

Any antibody fragment retaining the above criteria of a specific binding agent can be used. Antibodies are generated by state of the art procedures, e.g., as described in Tijssen (Tijssen, P., Practice and theory of enzyme immunoassays, 11, Elsevier Science Publishers B.V., Amsterdam, the whole book, especially pages 43-78). In addition, the skilled artisan is well aware of methods based on immunosorbents that can be used for the specific isolation of antibodies. By these means the quality of polyclonal antibodies and hence their performance in immunoassays can be enhanced (Tijssen, P., supra, pages 108-115).

For the achievements as disclosed in the present invention polyclonal antibodies raised in rabbits may be used. However, clearly also polyclonal antibodies from different species, e.g., sheep or goat, as well as monoclonal antibodies can also be used. Since monoclonal antibodies can be produced in any amount required with constant properties, they represent ideal tools in development of an assay for clinical routine. The generation and the use of monoclonal antibodies to DPPIV/seprase in a method according to the present invention, respectively, represent yet other preferred embodiments.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates, In: Practice and theory of enzyme immunoassays, pp. 221-278, Burdon, R. H. and v. Knippenberg, P. H. (eds.), Elsevier, Amsterdam (1990), and various volumes of "Methods in Enzymology" (Eds. S. P. Colowick, N. O. Caplan, Academic Press), dealing with immunological detection methods, especially volumes 70, 73, 74, 84, 92 and 121.

According to the present invention, the concentration of DPPIV/seprase is determined. In one embodiment, the marker DPPIV/seprase is specifically measured from a sample by use of a specific binding agent.

As the skilled artisan will appreciate now that the DPPIV/seprase has been identified as a marker which is useful in the assessment of cancer, preferably of lung or colon cancer. Various immunodiagnostic procedures may be used to reach a result comparable to the achievements of the present invention. For example, alternative strategies to generate antibodies may be used. Such strategies comprise amongst others the use of synthetic peptides, representing an epitope of DPPIV, seprase or DPPIV/seprase for immunization. Alternatively, DNA immunization also known as DNA vaccination may be used.

For measurement the sample obtained from an individual is incubated with the specific binding agents for the DPPIV/seprase under conditions appropriate for complex formation of a binding agent-DPPIV/seprase. Such conditions need not be specified, since the skilled artisan without any inventive effort can easily identify such appropriate incubation conditions. The amount of binding agent-DPPIV/seprase is measured and used in the assessment of cancer, preferably of lung cancer. As the skilled artisan will appreciate there are numerous methods to measure the amount of the specific binding agent-DPPIV/seprase all described in detail in relevant textbooks (cf., e.g., Tijssen, P., supra, or Diamandis, E. P., and Christopoulos, T. K. (eds.), Immunoassay, Academic Press, Boston (1996)).

Preferably, DPPIV/seprase is detected in a sandwich-type assay format (=sandwich immunoassay). In such sandwich immunoassay, a first specific binding agent attached to a solid support is used to capture DPPIV/seprase on the one side and a second specific binding agent, which is labeled to be directly or indirectly detectable, is used on the other side. The specific binding agents used in a sandwich-type assay format may be a combination of antibodies specifically directed against DPPIV and seprase, respectively.

Also preferred is a sandwich immunoassay with an capture antibody against soluble DPPIV and a detection antibody against soluble seprase, and vice versa.

Also preferred is a sandwich immunoassay with antibodies that bind the DPPIV/seprase complex but not the soluble DPPIV or soluble seprase.

In some diagnostic settings antibodies recognizing only the uncomplexed form of soluble DPPIV or soluble seprase may also be used.

A "marker of cancer" and in particular a "marker of lung cancer" and "marker of colon cancer" in the sense of the present invention is any marker that if combined with the marker DPPIV/seprase adds relevant information in the assessment of cancer, e.g., in the assessment of cancer in general or in the assessment of certain cancer types, e.g., in the assessment of LC or CRC. The information is considered relevant or of additive value if at a given specificity the sensitivity, or if at a given sensitivity the specificity, respectively, for the assessment of cancer can be improved by including said marker into a marker combination already comprising the marker DPPIV/seprase. In the preferred embodiment of cancer assessment, the improvement in sensitivity or specificity, respectively, is statistically significant at a level of significance of $p=0.05, 0.02, 0.01$ or lower. Preferably, the one or more other tumor marker is selected from the group consisting of Cyfra 21-1, CEA, FERR, OPN, anti-p53 autoantibodies, seprase, NNMT, PSE3, S100A12, CYBP, ASC, NSE, CA19-9 and CA125.

The term "sample" as used herein refers to a biological sample obtained for the purpose of evaluation in vitro. In the methods of the present invention, the sample or patient sample preferably may comprise any body fluid. Preferred test samples include blood, serum, plasma, sputum, ELF and BAL. Preferred samples are whole blood, serum, plasma, ELF, with plasma or serum being most preferred.

The term "assessing cancer" and in particular "assessing lung cancer" or "assessing colon cancer" is used to indicate that the method according to the present invention will (alone or together with other markers or variables, e.g., the criteria set forth by the UICC (see above)) e.g., aid the physician to establish or confirm the absence or presence of cancer, in particular of LC or of CRC or aid the physician in the prognosis, the detection of recurrence (follow-up of patients after surgery) and/or the monitoring of treatment, especially of chemotherapy.

As the skilled artisan will appreciate, any such assessment is made in vitro. The patient sample is discarded afterwards. The patient sample is solely used for the in vitro diagnostic method of the invention and the material of the patient sample is not transferred back into the patient's body. Typically, the sample is a liquid sample, e.g., whole blood, serum, or plasma.

Unless otherwise noted, technical terms are used according to conventional usage. Definitions of common terms in cell and molecular biology may be found in Lewin, B., Genes, V., published by Oxford University Press (1994), ISBN 0-19-854287 9; Kendrew, J. et al. (eds.), The Encyclopedia of Molecular Biology, published by Blackwell Science Ltd. (1994), ISBN 0-632-02182-9; and Meyers, R. A. (ed.), Molecular Biology and Biotechnology: a Comprehensive Desk Reference, published by VCH Publishers, Inc. (1995), ISBN 1-56081-569 8.

In a preferred embodiment the present invention relates to a method for assessing cancer, e.g., LC or CRC, in vitro by biochemical markers, comprising measuring in a sample the concentration of DPPIV/seprase and using the concentration determined in the assessment of cancer, e.g., LC or CRC.

The inventors of the present invention have surprisingly been able to detect a decreased concentration of the marker DPPIV/seprase in a significant percentage of samples derived from patients with cancer, in particular with lung, colon, head and neck, pancreas, esophagus, stomach, bile duct, kidney, cervix, ovary, breast, bladder, endometrium or prostate cancer. Even more surprising they have been able to demonstrate that the decreased concentration of DPPIV/seprase in such sample obtained from an individual can be used in the assessment of cancer, in particular of the above-mentioned cancer diseases.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case for many cancer types, e.g., for LC. As the skilled artisan will appreciate, no biochemical marker is diagnostic with 100% specificity and at the same time 100% sensitivity for a given multifactorial disease, for example for LC. Rather, biochemical markers, e.g., Cyfra 21-1, CEA, NSE, or as shown here DPPIV/seprase can be used to assess with a certain likelihood or predictive value e.g., the presence, absence, or the severity of a disease. Therefore in routine clinical diagnosis, generally various clinical symptoms and biological markers are considered together in the diagnosis, treatment and management of the underlying disease.

Biochemical markers can either be determined independently or in a preferred embodiment of the invention they can be measured simultaneously using a bio-chip or a bead based array technology. The concentrations of the biomarkers are then either interpreted independently, e.g., using an individual cut-off for each marker, or they are combined for interpretation.

In a further preferred embodiment the assessment of cancer according to the present invention is performed in a method comprising measuring in a sample the concentration of a) DPPIV/seprase, b) one or more other marker of cancer, and c) using the measurement result, e.g., the concentrations determined in step (a) and step (b), respectively, in the assessment of cancer.

In the assessment of cancer the marker DPPIV/seprase will be of advantage in one or more of the following aspects: screening; diagnostic aid; prognosis; monitoring of therapy such as chemotherapy, radiotherapy, and immunotherapy.

Screening

Screening is defined as the systematic application of a test to identify individuals, e.g., at risk individuals, for indicators of a disease, e.g., the presence of cancer. Preferably the screening population is composed of individuals known to be at higher than average risk of cancer. For example, a screening population for lung cancer is composed of individuals known to be at higher than average risk of lung cancer, like smokers, ex-smokers, and uranium-, quartz- or asbestos-exposed workers.

In the preferred embodiment, a body fluid such as whole blood, plasma, serum, sputum, epithelial lining fluid (ELF; preferred in the case of suspected LC) or bronchio alveolar lavage (BAL; preferred in the case of suspected LC) is used as a sample in the screening for cancer, e.g., lung or colorectal cancer.

For many diseases, no single biochemical marker in the circulation will ever meet the sensitivity and specificity criteria required for screening purposes. This appears to be also true for cancer and in particular for lung cancer. It has to be expected that a marker panel comprising a plurality of markers will have to be used in cancer screening. The data established in the present invention indicate that the marker DPPIV/seprase will form an integral part of a marker panel appropriate for screening purposes. The present invention therefore relates to the use of DPPIV/seprase as one marker of a cancer marker panel, i.e., a marker panel comprising DPPIV/seprase and one or more additional marker for cancer screening purposes. In particular, the present invention relates to the use of DPPIV/seprase as one marker of a general cancer marker panel. Such marker panel comprises the marker DPPIV/seprase and one or more additional markers, e.g., general cancer markers and/or markers for the above-mentioned type of cancer.

DPPIV/seprase is also likely to contribute to marker panels for certain specific types of cancer, e.g., lung, colon, head and neck, pancreas, esophagus, stomach, bile duct, kidney, cervix, ovary, breast, bladder, endometrium or prostate cancer.

Other preferred types of cancer to be assessed with a marker panel comprising DPPIV/seprase are lung, colon, head and neck or pancreas cancer.

Other preferred types of cancer to be assessed with a marker panel comprising DPPIV/seprase are lung (LC) or colon cancer (CRC).

A preferred type of cancer to be assessed with a marker panel comprising DPPIV/seprase is CRC.

A preferred type of cancer to be assessed with a marker panel comprising DPPIV/seprase is LC.

The present data further indicate that certain combinations of markers will be advantageous in the screening for cancer.

For example, with reference to the embodiment of screening cancer, the present invention also relates to the use of a marker panel comprising DPPIV/seprase and one or more other tumor markers selected from the group consisting of Cyfra 21-1, CEA, FERR, OPN, anti-p53 autoantibodies, seprase, NNMT, PSE3, S100A12, CYBP, ASC, NSE, CA19-9 and CA125.

For example, with reference to the embodiment of screening CRC, the present invention also relates to the use of a marker panel comprising DPPIV/seprase and one or more other tumor markers selected from the group consisting of Cyfra 21-1, CEA, FERR, OPN, anti-p53 autoantibodies, seprase, NNMT, PSE3, S100A12, CA19-9 and CA125.

For example, with reference to the embodiment of screening LC, the present invention also relates to the use of a marker panel comprising DPPIV/seprase and one or more other tumor markers selected from the group consisting of CYBP, NNMT, PSE3, ASC, OPN, seprase, S100A12, NSE, Cyfra 21-1, CEA, CA19-9 and CA125.

Diagnostic Aid

Markers may either aid the differential diagnosis of benign vs. malignant disease in a particular organ, help to distinguish between different histological types of a tumor, or to establish baseline marker values before surgery.

In a preferred embodiment the marker DPPIV/seprase is used in an immunohistological method in order to establish or confirm different histological types of cancer.

Since DPPIV/seprase as a single marker might be superior to other markers, e.g., in the case of LC to other markers, like CEA or NSE, it has to be expected that DPPIV/seprase will be used as a diagnostic aid, especially by establishing a baseline value before surgery. The present invention thus also relates to the use of DPPIV/seprase for establishing a baseline value before surgery for cancer.

Prognosis

Prognostic indicators can be defined as clinical, pathological, or biochemical features of cancer patients and their tumors that predict with a certain likelihood the disease outcome. Their main use is to help to rationally plan patient management, i.e., to avoid undertreatment of aggressive disease and overtreatment of indolent disease, respectively. Molina, R. et al., Tumor Biol. 24 (2003) 209-218 evaluated the prognostic value of CEA, CA 125, Cyfra 21-1, SSC and NSE, in NSCLC. In their study abnormal serum levels of the markers NSE, CEA, and LDH (lactate dehydrogenase) appeared to indicate shorter survival.

As DPPIV/seprase alone significantly contributes to the differentiation of cancer patients, e.g., LC or CRC patients, from healthy controls, it has to be expected that it will aid in assessing the prognosis of patients suffering from cancer, preferably from LC or CRC. The level of preoperative DPPIV/seprase will most likely be combined with one or more other marker for cancer and/or the TNM staging system. In a preferred embodiment DPPIV/seprase is used in the prognosis of patients with LC or CRC.

Monitoring of Therapy

Merle, P. et al., Int. J. of Biological Markers 19 (2004) 310-315 have evaluated Cyfra 21-1 serum level variations in patients with locally advanced NSCLC treated with induction chemotherapy. They conclude that early monitoring of Cyfra 21-1 serum levels may be a useful prognostic tool for tumor response and survival in stage III NSCLC patients. In addition, reports have described the use of CEA in monitoring the treatment of patients with LC (Fukasawa, T. et al., Gan to Kagku Ryoho 13 (1986) 1862-1867). Most of these studies were retrospective, non-randomized and contained small numbers of patients. As in the case of the studies with Cyfra 21-1 the CEA studies suggested: a) that patients with a decrease in CEA levels while receiving chemotherapy generally had a better outcome than those patients whose CEA levels failed to decrease and (b) for almost all patients, increases in CEA levels were associated with disease progression.

It is expected that DPPIV/seprase will be at least as good a marker for monitoring of chemotherapy as Cyfra 21-1 or CEA, respectively. The present invention therefore also relates to the use of DPPIV/seprase in the monitoring of cancer patients and preferably of LC or CRC patients under therapy.

In the monitoring of therapy in one preferred embodiment the measurements for DPPIV/seprase and for at least one marker selected from the group consisting of CYBP, NNMT, PSE3, ASC, OPN, seprase, S100A12, NSE, CEA, Cyfra 21-1, CA 19-9 and CA 125 will be combined and used in the assessment of LC.

In the monitoring of therapy in one preferred embodiment the measurements for DPPIV/seprase and for at least one marker selected from the group consisting of CEA, Cyfra 21-1, Feritin, OPN, anti-p53 autoantibodies, NNMT, PSE3, S100A12, CA 19-9 and CA 125 will be combined and used in the assessment of CRC.

Follow-Up

A large portion of LC patients who undergo surgical resection aimed at complete removal of cancerous tissue later develop recurrent or metastatic disease (Wagner, H. Jr., Chest 117 (2000) 110S-118S; Buccheri, G. et al., Ann. Thorac. Surg. 75 (2003) 973-980). Most of these relapses occur within the first 2-3 years after surgery. Since recurrent/metastatic disease is invariably fatal if detected too late, considerable research has focused on cancer relapse at an early and thus potentially treatable stage.

Consequently, many cancer patients, e.g., LC patients undergo a postoperative surveillance program which frequently includes regular monitoring with CEA. Serial monitoring with CEA one year after surgical resection has been shown to detect an early postoperative recurrent/metastatic disease with a sensitivity of approximately 29%, at a specificity of approximately 97%, even in the absence of suspicious symptoms or signs (Buccheri, G., et al., Ann. Thorac. Surg. 75 (2003) 973-980). Thus, the follow-up of patients with LC after surgery is one of the most important fields of use for an appropriate biochemical marker. Due to the high sensitivity of DPPIV/seprase in the LC patients investigated it is likely that DPPIV/seprase alone or in combination with one or more other marker will be of great help in the follow-up of LC patients, especially in LC patients after surgery. The use of a marker panel comprising DPPIV/seprase and one or more other marker of LC in the follow-up of LC patients represents a further preferred embodiment of the present invention.

The present invention in a preferred embodiment relates to the use of DPPIV/seprase in the diagnostic field of cancer. Preferably DPPIV/seprase is used in the assessment of lung (LC), colon (CRC), esophagus, head and neck, stomach, bile duct, pancreas, kidney, cervix, ovary, breast, bladder, endometrium or prostate cancer, respectively.

In yet a further preferred embodiment the present invention relates to the use of DPPIV/seprase as a marker molecule for cancer, e.g., for cancer in general or for specific types of cancer, such as lung, colon, head and neck, pancreas, esophagus, stomach, bile duct, kidney, cervix, ovary, breast, bladder, endometrium or prostate cancer in combination with one or more further marker molecules for cancer. The further marker molecules may be cancer-type unspecific general marker molecules and/or cancer-type specific marker molecules, e.g., marker molecules for LC or CRC. DPPIV/seprase and the at least one further marker are used in the assessment of cancer, e.g., LC or CRC in a liquid sample obtained from an individual. Preferred selected other cancer markers with which the measurement of DPPIV/seprase may be combined are Cyfra 21-1, CEA, FERR, OPN, anti-p53 autoantibodies, seprase, NNMT, PSE3, S100A12, CYBP, ASC, NSE, CA19-9 and CA125. In particular, preferred selected other LC or CRC markers with which the measurement of DPPIV/seprase may be combined are Cyfra 21-1, CEA and/or NSE. Yet further preferred the marker panel used in the assessment of cancer, e.g., LC comprises DPPIV/seprase and at least one other marker molecule selected from the group consisting of Cyfra 21-1 and CEA.

As the skilled artisan will appreciate there are many ways to use the measurements of two or more markers in order to improve the diagnostic question under investigation. In a quite simple, but nonetheless often effective approach, a positive result is assumed if a sample is positive for at least one of the markers investigated. This may be, e.g., the case when diagnosing an infectious disease like AIDS.

Frequently, however, the combination of markers is evaluated. Preferably the values measured for markers of a marker panel, e.g., for DPPIV/seprase and Cyfra 21-1, are mathematically combined and the combined value is correlated to the underlying diagnostic question. Marker values may be combined by any appropriate state of the art mathematical method. Well-known mathematical methods for correlating a marker combination to a disease employ methods like, discriminant analysis (DA) (i.e., linear-, quadratic-, regularized-DA), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting/Bagging Methods), Generalized Linear Models (i.e., Logistic Regression), Principal Components based Methods (i.e., SIMCA), Generalized Additive Models, Fuzzy Logic based Methods, Neural Networks and Genetic Algorithms based Methods. The skilled artisan will have no problem in selecting an appropriate method to evaluate a marker combination of the present invention. Preferably the method used in correlating the marker combination of the invention e.g., to the absence or presence of LC is selected from DA (i.e., Linear-, Quadratic-, Regularized Discriminant Analysis), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting Methods), or Generalized Linear Models (i.e., Logistic Regression). Details relating to these statistical methods are found in the following references: Ruczinski, I. et al, J. of Computational and Graphical Statistics, 12 (2003) 475-511; Friedman, J. H., J. of the American Statistical Association 84 (1989) 165-175; Hastie, T. et al., The Elements of Statistical Learning, Springer Series in Statistics (2001); Breiman, L. et al., Classification and regression trees, California: Wadsworth (1984); Breiman, L., Random Forests, Machine Learning 45 (2001) 5-32; Pepe, M. S., The Statistical Evaluation of Medical Tests for Classification and Prediction, Oxford Statistical Science Series 28 (2003); and Duda, R. O. et al., Pattern Classification, Wiley Interscience, 2nd edition (2001).

It is a preferred embodiment of the invention to use an optimized multivariate cut-off for the underlying combination of biological markers and to discriminate state A from state B, e.g., diseased from healthy. In this type of analysis the markers are no longer independent but form a marker panel.

Accuracy of a diagnostic method is best described by its receiver-operating characteristics (ROC; see especially Zweig, M. H., and Campbell, G., Clin. Chem. 39 (1993) 561-577). The ROC graph is a plot of all of the sensitivity/specificity pairs resulting from continuously varying the decision threshold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1−specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1−specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1−specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One preferred way to quantify the diagnostic accuracy of a laboratory test is to express its performance by a single number. Such an overall parameter e.g., is the so-called "total error" or alternatively the "area under the curve=AUC". The most common global measure is the area under the ROC plot. By convention, this area is always >0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Combining measurements of DPPIV/seprase with other markers like Cyfra 21-1 or CEA, or with other markers of cancer yet to be discovered, DPPIV/seprase leads and will lead, respectively, to further improvements in assessment of cancer.

In a further preferred embodiment the present invention relates to a method for improving the diagnostic accuracy for cancer, e.g., LC or CRC versus healthy controls by measuring in a sample the concentration of at least DPPIV/seprase and one or more other tumor markers selected from the group consisting of Cyfra 21-1, CEA, FERR, OPN, anti-p53 autoantibodies, seprase, NNMT, PSE3, S100A12, CYBP, ASC, NSE, CA19-9 and CA125, respectively and correlating the concentrations determined to the presence or absence of cancer, e.g., LC or CRC, the improvement resulting in more patients being correctly classified as suffering from cancer, e.g., LC or CRC versus healthy controls as compared to a classification based on any single marker investigated alone.

In a preferred embodiment the present invention relates to a method for improving the diagnostic accuracy for cancer, e.g., LC or CRC versus healthy controls by measuring in a sample the concentration of at least DPPIV/seprase and Cyfra 21-1, and optionally of CEA and/or NSE, respectively and correlating the concentrations determined to the presence or absence of cancer, e.g., LC or CRC, the improvement resulting in more patients being correctly classified as suffering from cancer, e.g., LC or CRC versus healthy controls as compared to a classification based on any single marker investigated alone.

The following examples, sequence listing and figures are provided to aid the understanding of the present invention, the true scope of which is set forth in the appended claims.

It is understood that modifications can be made in the procedures set forth without departing from the spirit of the invention.

Example 1

Rat monoclonal anti-DPPIV and anti-seprase antibodies (clones E26 and D28, respectively) were purchased from Vitatex Inc. (Stony Brook, N.Y., USA). The antibodies were described previously by Ghersi, G. et al. (J. Biol. Chem. 277 (2002) 29231-29241) and Pineiro-Sanchez, M.-L. et al. (J. Biol. Chem. 12 (1997) 7595-7601).

Biotinylation of Monoclonal Rat IgG

Monoclonal rat IgG (clone E26) was brought to 10 mg/ml in 10 mM NaH2PO4/NaOH, pH 7.5, 30 mM NaCl. Per ml IgG solution 50 µl Biotin-N-hydroxysuccinimide (3.6 mg/ml in DMSO) were added. After 30 min at room temperature, the sample was chromatographed on Superdex 200 (10 mM NaH2PO4/NaOH, pH 7.5, 30 mM NaCl). The fraction containing biotinylated IgG were collected.

Digoxygenylation of Monoclonal Rat IgG

Monoclonal rat IgG (clone D28) was brought to 10 mg/ml in 10 mM NaH2PO4/NaOH, 30 mM NaCl, pH 7.5. Per ml IgG solution 50 µl digoxigenin-3-O-methylcarbonyl-s-aminocaproic acid-N-hydroxysuccinimide ester (Roche Diagnostics, Mannheim, Germany, Cat. No. 1 333 054) (3.8 mg/ml in DMSO) were added. After 30 min at room temperature, the sample was chromatographed on Superdex® 200 (10 mM NaH2PO4/NaOH, pH 7.5, 30 mM NaCl). The fractions containing digoxigenylated IgG were collected.

Example 2: ELISA for the Measurement of DPPIV/Seprase in Human Serum and Plasma Samples For detection of DPPIV/seprase in human serum or plasma, a sandwich ELISA was developed. For capture and detection of the antigen, aliquots of the anti-DPPIV monoclonal antibodies E26 and anti-seprase monoclonal antibodies D28 (see Example 1) were conjugated with biotin and digoxygenin, respectively.

Samples (20 µl) were mixed in separate wells of a streptavidin-coated microtiter plate with 100 µl of antibody reagent containing 0.12 µg/ml of each, E26-biotin and D28-digoxigenin antibodies in incubation buffer (40 mM phosphate, 200 mM sodium tartrate, 10 mM EDTA, 0.05% phenol, 0.1% polyethylene glycol 40000, 0.1% Tween 20, 0.2% BSA, 0.1% bovine IgG, 0.02% 5-Bromo-5-Nitro-1,3-Dioxane adjusted to pH 7.4, supplemented with 200 µg/ml polymeric monoclonal mouse IgG Fab-fragments for elimination of human anti-rat antibody response (HARA); Roche Diagnostics GmbH, Mannheim, Germany, Catalog #11096478-001).

After incubation for one hour plates were washed three times with washing buffer (10 mM Tris, 150 mM NaCl, 0.05% Tween 20).

In a next step, wells were incubated with 30 mU/ml anti-digoxigenin-HRP conjugate (Roche Diagnostics GmbH, Mannheim, Germany, Catalog #1633716) in Universal Conjugate Buffer (Roche Diagnostics GmbH, Mannheim, Germany, Catalog #11684825) for 60 min and washed as before.

Wells were then incubated for 30 min. with 100 µl of TMB substrate solution (Roche Diagnostics GmbH, Mannheim, Germany, Catalog #12034425). Adding of 2N sulfuric acid (50 µl) stopped the color development and switched the blue color into yellow. OD was measured at 450 nm with an ELISA reader.

All incubations were at room temperature. Samples of human serum or plasma were pre-diluted with incubation buffer ad 5%. For calibration, a human serum was used as a standard. It was diluted with incubation buffer ad 2/4/8/16/32% to make calibrators with arbitrarily given values of 2/4/8/16/32 Units/ml, respectively.

The equation of the calibration curve was calculated by non-linear least-squares curve-fitting (Wiemer-Rodbard) and used for converting the absorbance reading of a well into the corresponding concentration value. The result was multiplied by the pre-dilution factor to get the concentration of the respective sample itself.

Example 3: CRC Study Population

In a first study, samples derived from 48 well-characterized patients with colorectal cancer (UICC classification given in Table 1) have been used.

TABLE 1

| Stage according to UICC | Number of samples |
|---|---|
| UICC I | 6 |
| UICC II | 14 |
| UICC III | 13 |
| UICC IV | 6 |
| without staging | 9 |
| total number of CRC samples | 48 |

The samples of Table 1 have been evaluated in comparison with control samples obtained from 50 obviously healthy individuals without any known malignant disease (control cohort).

Figure 2:
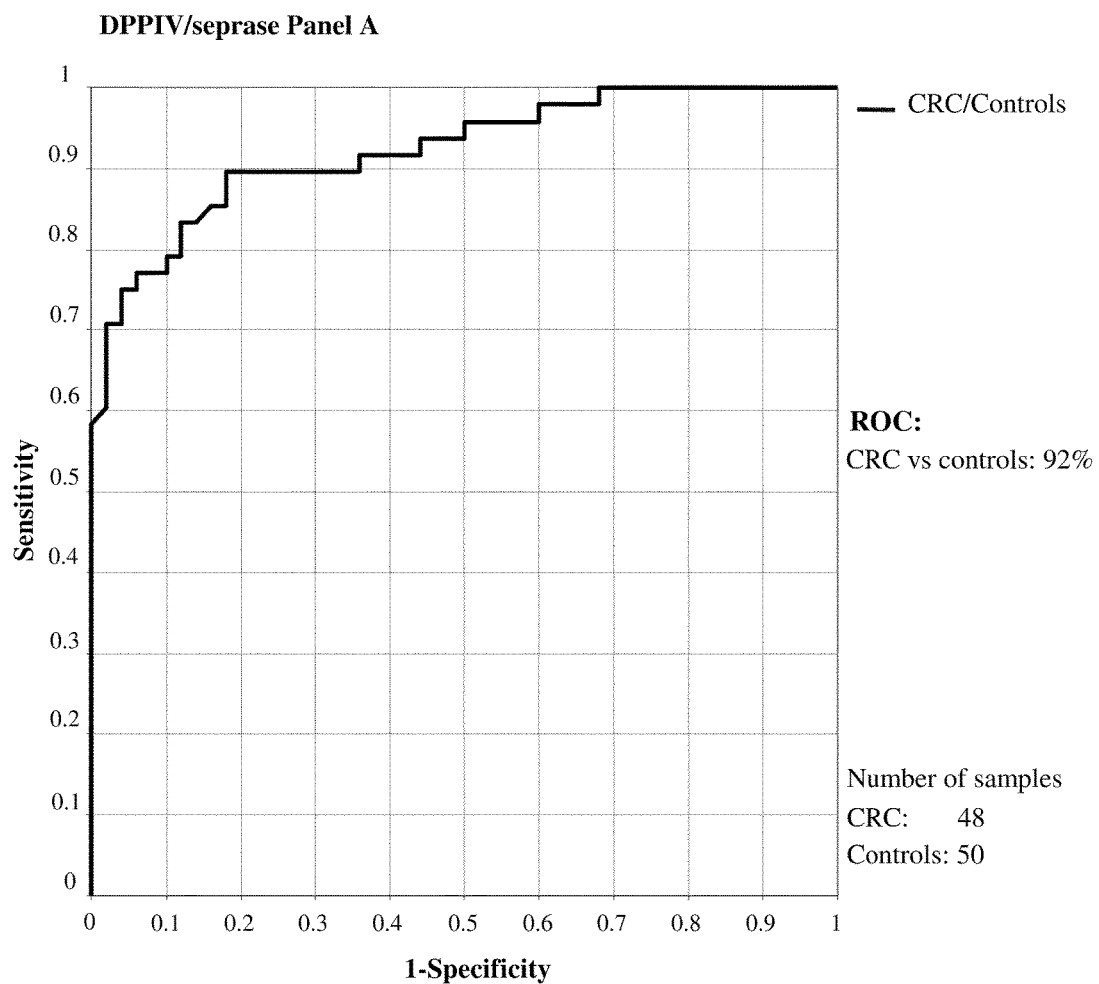
FIG. 2 shows the ROC curve of DPPIV/seprase test of the cohorts of CRC patients and healthy controls.

Example 4: DPPIV/Seprase Complex Discriminates Cancer Patients from Healthy Controls The serum concentration of DPPIV/seprase differs markedly between CRC patients and healthy controls (FIGS. 1 and 2).

The mean concentration of the CRC patient cohorts is significantly lower than that of the control cohorts: 51.6 U/ml in patients vs. 85.8 U/ml in controls. With a cut-off value that yields 95% specificity on the respective control cohort, the sensitivity for colorectal cancer is 75%.

The sensitivity is similar for all stages of cancer (Table 2). Therefore, DPPIV/seprase concentration in serum/plasma can be used as an early indicator of disease.

TABLE 2

CRC study: sensitivity depending on UICC classification

| Stage according to UICC | Number of samples | Number positive | % Positive |
|---|---|---|---|
| UICC I | 6 | 5 | 83 |
| UICC II | 14 | 12 | 86 |
| UICC III | 13 | 8 | 61.5 |
| UICC IV | 6 | 5 | 83 |
| without staging | 9 | 5 | 55 |
| total number of CRC samples | 48 | | |

Example 5: LC Study Population

A second study totally independent from the first one focused on lung cancer (precisely non small cell lung cancer: NSCLC), head and neck and pancreatic cancers. For NSCLC, patients suffering from its two main types, adenocarcinoma and squamous cell carcinoma were investigated. Table 3 describes the type and stage distribution of the lung cancer cohort.

TABLE 3

Type and staging of LC samples

|  | Number of samples | |
| --- | --- | --- |
| Type of cancer | UICC I or II | UICC III or IV |
| Adenocarcinoma | 12 | 17 |
| Squamous cell carcinoma | 12 | 18 |
| total number of NSCLC samples | 57 | |

The control cohort in this study was defined especially to comprise samples from smokers and non-smokers as described in Table 4. A spirometry lung function testing (Miller, M. R. et al., Eur. Respir. J. 26 (2005) 319-338) was carried out with each individual. Samples were included in the control cohort only if the donor's result was within the normal range. The same control cohort was applied for evaluation of DPPIV/seprase test sensitivities for head and neck and pancreatic cancers.

TABLE 4

Composition of the control cohort

| Individuals | Number of samples |
| --- | --- |
| Smokers | 30 |
| Ex-smokers | 5 |
| Non-smokers | 25 |
| Not specified | 7 |

Example 6: DPPIV/Seprase Discriminates LC Patients from Healthy Controls

Figure 3:
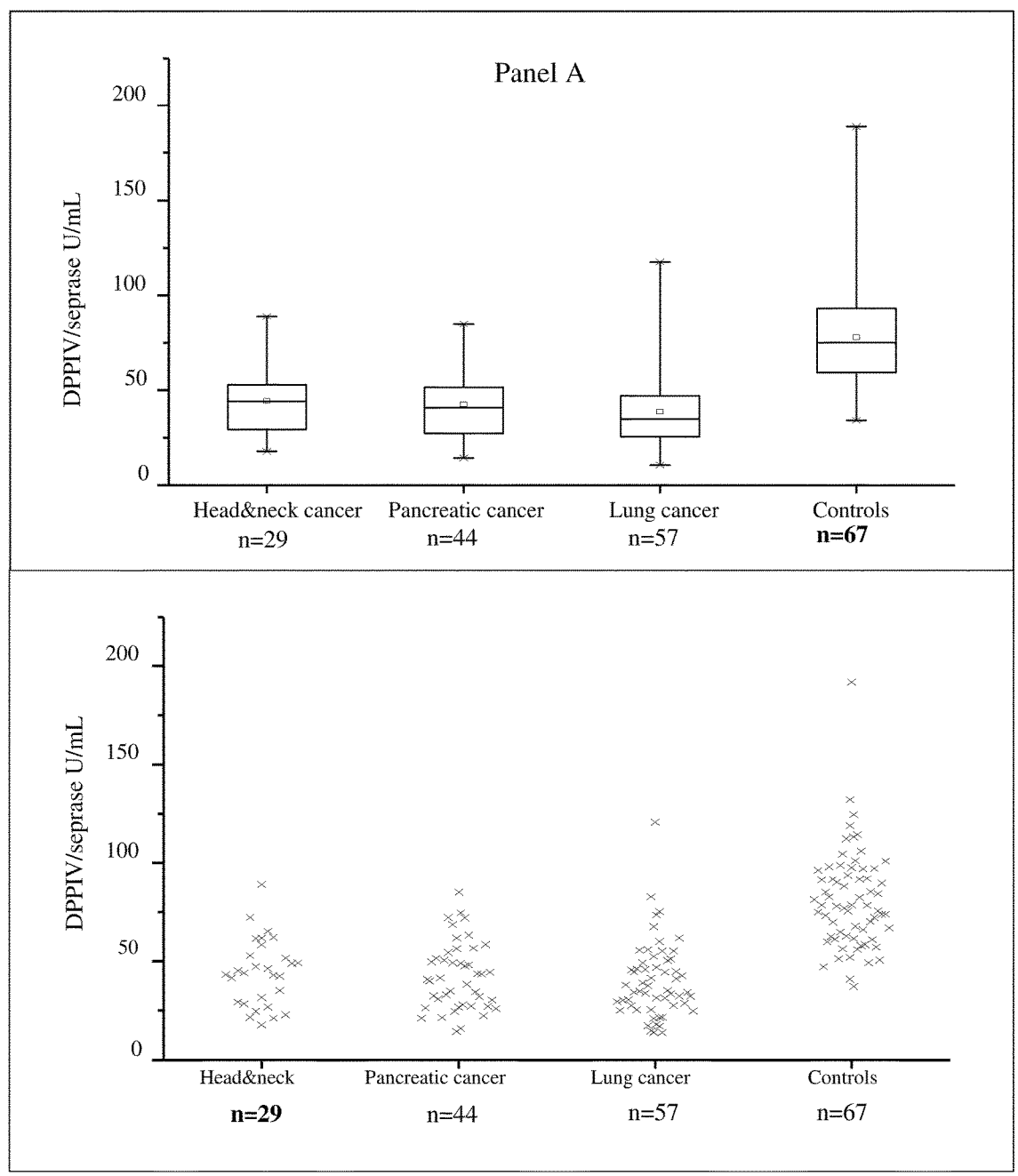
FIG. 3 shows the distribution of DPPIV/seprase values within the cohorts of LC, head and neck- and pancreatic cancer patients and healthy controls.
Figure 4:
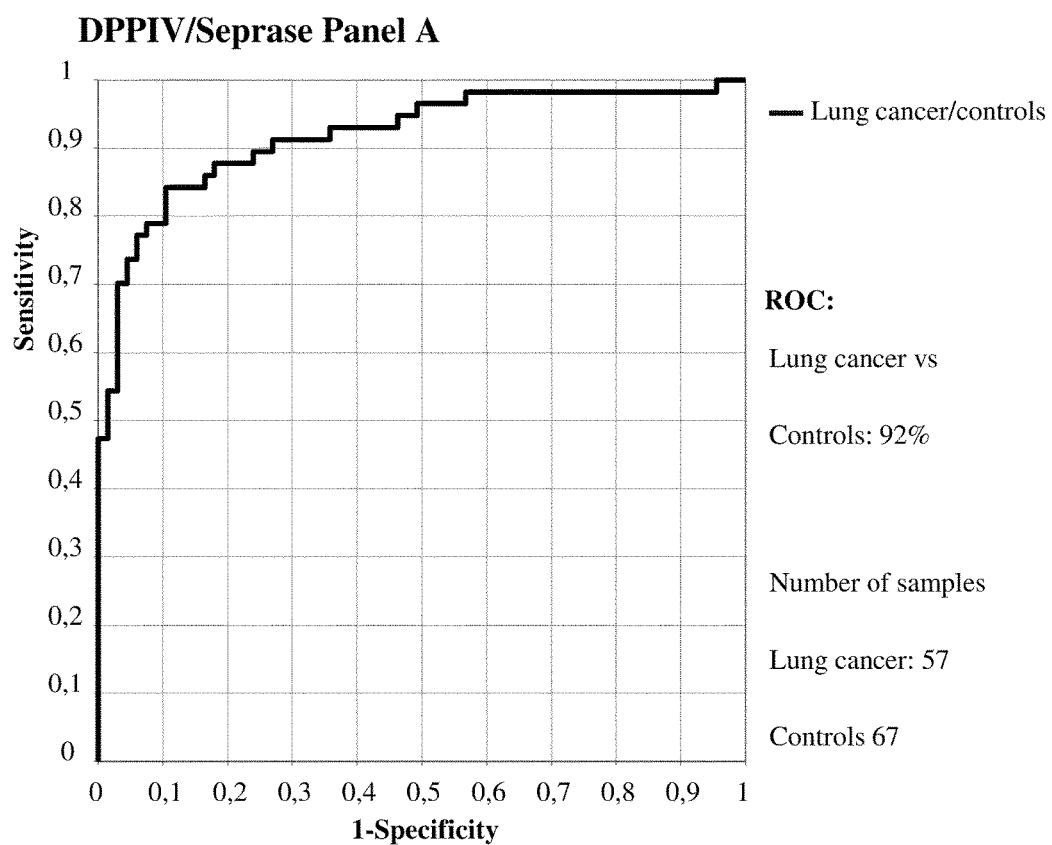
FIG. 4 shows the ROC curve of DPPIV/seprase test of the cohorts of LC patients and healthy controls.
Figure 5:
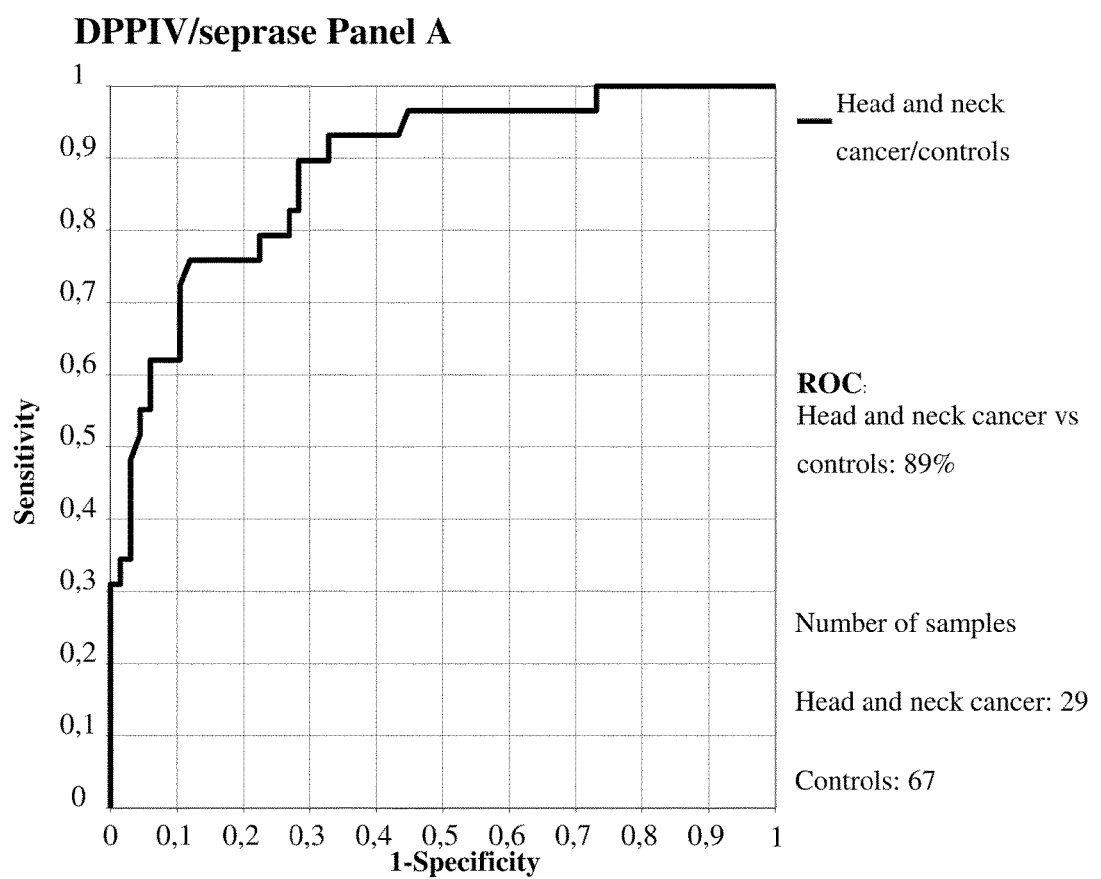
FIG. 5 shows the ROC curve of DPPIV/seprase test of the cohorts of head and neck cancer patients and healthy controls.
Figure 6:
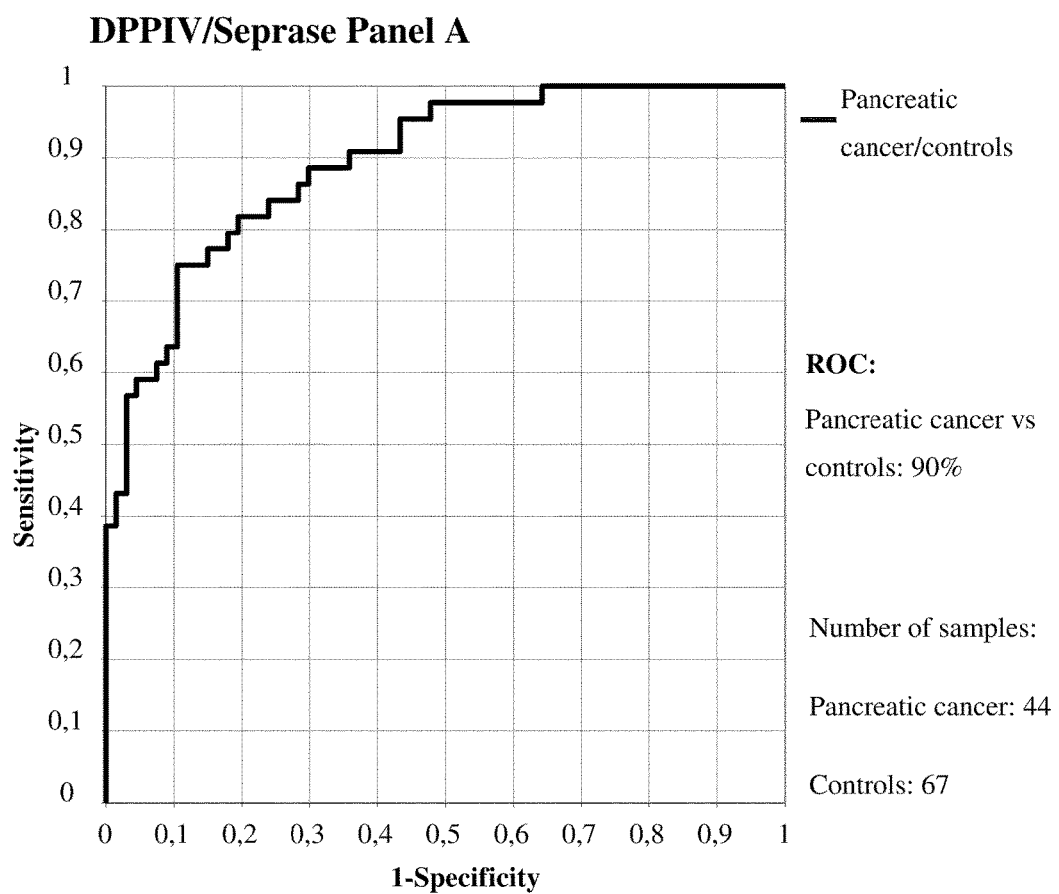
FIG. 6 shows the ROC curve of DPPIV/seprase test of the cohorts of pancreatic cancer patients and healthy controls.

The serum concentration of DPPIV/seprase differs markedly between LC patients and healthy controls (FIG. 3). The mean concentration of the cancer patient cohorts is significantly lower than that of the control cohorts: 35 U/ml in patients vs. 75 U/ml in controls. With a cut-off value that yields 95% specificity on the respective control cohort, the sensitivity for lung cancer is 77%.

The sensitivity is similar for all stages of lung cancer, while the sensitivity for squamous cell carcinoma is higher than for adenocarcinoma (Table 5).

TABLE 5

LC study: Sensitivity depending on type and staging

| Stage and type of LC | Number of samples | Number positive | % positive |
| --- | --- | --- | --- |
| UICC I and II | 24 | 18 | 75 |
| UICC III and IV | 33 | 26 | 79 |
| Adenocarcinoma | 29 | 21 | 72 |
| Squamous cell carcinoma | 28 | 23 | 82 |
| Total LC samples | 57 | 44 | 77 |

Example 7: Head and Neck Study Population

In this study samples derived from 29 well-characterized patients with head and neck cancer have been used (UICC classification given in Table 6). The samples have been evaluated in comparison with control samples obtained from 67 obviously healthy individuals without any known malignant disease (control cohort). The same control cohort was applied for evaluation of DPPIV/seprase test sensitivities for LC and pancreatic cancers.

TABLE 6

Type and staging of head and neck cancer samples

| Stage according to UICC | Number of samples |
| --- | --- |
| UICC I | 2 |
| UICC II | 2 |
| UICC III | 2 |
| UICC IV | 21 |
| without staging | 2 |
| total head and neck cancer samples | 29 |

Example 8: DPPIV/Seprase Discriminates Head and Neck Cancer Patients from Healthy Controls The serum concentration of DPPIV/seprase differs between head and neck cancer patients and healthy controls (FIG. 3). The mean concentration of the head and neck cancer patient cohorts is significantly lower than that of the control cohorts: 44 U/ml in patients vs. 75 U/ml in controls. With a cut-off value that yields 95% specificity on the respective control cohort, the sensitivity for head and neck cancer is 59%.

Example 9: Pancreatic Cancer Study Population

In this study samples derived from 44 well-characterized patients with pancreatic cancer have been evaluated in comparison with control cohort. The same control cohort was applied for evaluation of DPPIV/seprase test sensitivities for LC and head and neck cancers. Table 7 describes the type and stage distribution of the pancreatic cancer cohort.

TABLE 7

Type and staging of pancreatic cancer samples

| Stage according to UICC | Number of samples |
| --- | --- |
| UICC I | 0 |
| UICC II | 24 |
| UICC III | 5 |
| UICC IV | 13 |
| without staging | 2 |
| total pancreatic cancer samples | 44 |

Example 10: DPPIV/Seprase Complex Discriminates Pancreatic Cancer Patients from Healthy Controls The serum concentration of DPPIV/seprase differs markedly between pancreatic cancer patients and healthy controls (FIG. 3). The mean concentration of the pancreatic cancer patient cohorts is significantly lower than that of the control cohorts: 41 U/ml in patients vs. 75 U/ml in controls. With a cut-off value that yields 95% specificity on the respective control cohort, the sensitivity for pancreatic cancer is 59%.

What is claimed is:

1. An immunoassay method for determining an amount of soluble dipeptidyl peptidase IV/seprase protein complex (DPPIV/seprase complex) in a serum or plasma sample, the method comprising the steps of: combining the sample suspected of containing DPPIV/seprase complex with monoclonal antibody E26 specific for DPPIV and monoclonal antibody D28 specific for seprase under conditions appropriate for formation of an antibody-DPPIV/seprase complex; measuring via enzyme-linked immunosorbent assay (ELISA) the antibody-DPPIV/seprase complex by adding a detection moiety which binds to the antibody-DPPIV/seprase complex; and quantifying an amount of DPPIV/seprase complex in the sample based on said step of measuring.

2. The method of claim 1, wherein either the monoclonal antibody E26 specific for DPPIV or the monoclonal antibody D28 specific for seprase is bound directly or indirectly to a solid support.

3. An in vitro method for detecting a concentration of DPPIV/seprase complex in a patient suspected of having cancer, the method comprising: contacting a portion of a serum or plasma sample from the patient with an antibody having specific binding affinity for soluble dipeptidyl peptidase IV/seprase protein complex (DPPIV/seprase) selected from monoclonal antibody E26 having specific binding affinity for human soluble DPPIV and monoclonal antibody D28 having specific binding affinity for human soluble seprase, thereby forming a complex between the antibody and the DPPIV/seprase, the antibody having a detectable label; separating the complex formed in said step of contacting from antibody not comprising the complex; quantifying a signal from the detectable label of the antibody comprising the complex formed in said step of contacting, the signal being proportional to an amount of DPPIV/seprase in the sample, whereby a concentration of DPPIV/seprase in the sample is calculated; measuring the concentration of an additional biomarker, the additional biomarker selected from the group consisting of: CYBP, nicotinamide N-methyltransferase (NNMT), apoptosis-associated speck-like protein containing a caspase-associated recruitment domain (ASC), osteopontin (OPN), seprase, S100A12, neuron-specific enolase (NSE), ferritin (FERR), anti-p53 autoantibodies, CA125 and cytokeratin 19 fragment (cyfra 21-1).

4. The method according to claim 3, further comprising the step of measuring in a portion of the sample from the patient a concentration of a second additional marker selected from the group consisting of carcinoembryonic antigen (CEA), PSE3, and CA19-9.

5. The method according to claim 3, wherein the antibody has specific binding affinity for the one of human soluble DPPIV and human soluble seprase only when comprising soluble dipeptidyl peptidase IV/seprase protein complex (DPPIV/seprase).

6. The method according to claim 3, wherein the detectable label comprises one of a colorimetric label, a fluorescent label and a protein label.

7. The method according to claim 6, wherein the detectable label comprises a peroxidase conjugate.

8. The method according to claim 6, wherein the detectable label comprises digoxigenin.

9. The method according to claim 3, wherein the DPPIV/seprase reference concentration has a specificity of at least 90%.

10. The method according to claim 3 further comprising providing a diagnosis of one of lung cancer, colorectal cancer, head and neck cancer and pancreatic cancer in the patient if the concentration of DPPIV/seprase in the sample calculated in said step of quantifying is less than a DPPIV/seprase reference concentration.

11. The method according to claim 3, wherein the patient has or is suspected of having one of lung cancer, colorectal cancer, head and neck cancer and pancreatic cancer.

12. An in vitro method for diagnosing one of lung cancer, colorectal cancer, head and neck cancer and pancreatic cancer in a patient classified as at least one of suspected of having recurrent cancer and suspected of having a tumor, the method comprising: contacting a portion of a serum or plasma sample obtained from the patient with a capture antibody selected from monoclonal antibody E26 and monoclonal antibody D28 having specific binding affinity for a first epitope of soluble dipeptidyl peptidase IV/seprase protein complex (DPPIV/seprase) and with a detection antibody selected from monoclonal antibody E26 and monoclonal antibody D28 having specific binding affinity for a second epitope of DPPIV/seprase, thereby forming a complex of the capture antibody, DPPIV/seprase and the detection antibody, the first epitope being different than the second epitope, the capture antibody coupled to one of avidin, biotin and a solid support, the detection antibody having a detectable label; contacting the complex of the capture antibody, the DPPIV/seprase and detection antibody with a solid support, whereby the complex couples to the solid support; separating the complex of the capture antibody, the DPPIV/seprase and detection antibody coupled to the solid support from capture antibody, detection antibody and DPPIV/seprase not coupled to the solid support; exposing the complex of the capture antibody, DPPIV/seprase and detection antibody to a substrate, thereby producing a signal from the detectable label of the detection antibody comprising the complex separated from capture antibody, detection antibody and DPPIV/seprase not coupled to the solid support in said step of separating; quantifying the signal produced in said step of exposing, the signal being proportional to an amount of DPPIV/seprase in the sample from the individual, whereby a concentration of DPPIV/seprase in the sample is calculated; comparing the concentration of DPPIV/seprase calculated in said step of quantifying to a DPPIV/seprase reference concentration, the DPPIV/seprase reference concentration being calculated from a group of more than one unaffected patient; and providing a diagnosis of one of lung cancer, colorectal cancer, head and neck cancer and pancreatic cancer in the patient if the concentration of DPPIV/seprase in the sample calculated in said step of quantifying is less than the DPPIV/seprase reference concentration.

13. The method according to claim 12, wherein the detectable label comprises one of a colorimetric label, a fluorescent label and a protein label.

14. The method according to claim 13, wherein the detectable label comprises a peroxidase conjugate.

15. The method according to claim 13, wherein the detectable label comprises digoxigenin.

16. The method according to claim 12, wherein the DPPIV/seprase reference concentration has a specificity of at least 90%.

17. The method according to claim 12, wherein the solid support comprises one of a bead or a bio-chip.

* * * * *